United States Patent
Hinman et al.

(10) Patent No.: US 11,786,290 B2
(45) Date of Patent: Oct. 17, 2023

(54) UNIVERSAL HANDPIECE FOR ELECTRICAL TREATMENT APPLICATOR

(71) Applicant: Pulse Biosciences, Inc., Hayward, CA (US)

(72) Inventors: Cameron D. Hinman, Thurmond, NC (US); Kevin L. Moss, Lathrop, CA (US); Wesley C. Joe, Mountain View, CA (US); Peter H. Robino, Hayward, CA (US)

(73) Assignee: Pulse Biosciences, Inc., Hayward, CA (US)

( * ) Notice: Subject to any disclaimer, the term of this patent is extended or adjusted under 35 U.S.C. 154(b) by 0 days.

(21) Appl. No.: 17/590,790

(22) Filed: Feb. 1, 2022

(65) Prior Publication Data
US 2022/0151679 A1    May 19, 2022

Related U.S. Application Data

(63) Continuation of application No. PCT/US2021/047879, filed on Aug. 27, 2021.
(Continued)

(51) Int. Cl.
*A61B 18/12* (2006.01)
*A61B 18/00* (2006.01)
*A61B 18/14* (2006.01)

(52) U.S. Cl.
CPC .............. *A61B 18/1233* (2013.01); *A61B 2018/00178* (2013.01); *A61B 2018/00755* (2013.01);
(Continued)

(58) Field of Classification Search
CPC ...... A61B 18/1233; A61B 2018/00178; A61B 2018/00755; A61B 2018/1425; A61B 2018/1467
See application file for complete search history.

(56) References Cited

U.S. PATENT DOCUMENTS 5,817,092 A * 10/1998 Behl .................. A61B 18/1477
606/1
6,326,177 B1   12/2001 Schoenbach et al.
(Continued)

FOREIGN PATENT DOCUMENTS

CN        102542175 B      8/2014

OTHER PUBLICATIONS

Gundersen et al.; Nanosecond pulse generator using a fast recovery diode; IEEE; InProceedings of the 26th Inernational Pulsed Modulator Conference: 603-606; (year of pub. sufficiently earlier than effective US filing date and any foreign priority date) 2004.
(Continued)

*Primary Examiner* — Michael F Peffley
*Assistant Examiner* — Bo Ouyang
(74) *Attorney, Agent, or Firm* — Shay Glenn LLP

(57) ABSTRACT

Methods and apparatuses (e.g., devices, instruments and systems, including applicator handles for use with pulse generators) for automatically and/or mechanically setting impedance matching for connecting the applicator handle with different electrode tips. These methods and apparatuses may be useful for applying therapeutic energy, including but not limited to short, high field strength electric pulses, while avoiding the risk of arcing or otherwise harming the tissue.

27 Claims, 18 Drawing Sheets

Related U.S. Application Data

(60) Provisional application No. 63/073,907, filed on Sep. 2, 2020.

(52) U.S. Cl.
CPC ............... *A61B 2018/1425* (2013.01); *A61B 2018/1467* (2013.01)

(56) References Cited

U.S. PATENT DOCUMENTS

| | | |
|---|---|---|
| 6,478,030 B1 | 11/2002 | Shapeton et al. |
| 6,831,377 B2 | 12/2004 | Yampolsky et al. |
| 7,767,433 B2 | 8/2010 | Kuthi et al. |
| 8,000,813 B2 | 8/2011 | Schoenbach et al. |
| 8,512,334 B2 | 8/2013 | Nuccitelli et al. |
| 8,702,691 B2 * | 4/2014 | Weber ............... A61B 18/14 606/41 |
| 8,822,222 B2 | 9/2014 | Beebe et al. |
| 9,101,764 B2 | 8/2015 | Nuccitelli et al. |
| 9,724,155 B2 | 8/2017 | Nuccitelli et al. |
| 10,850,095 B2 | 12/2020 | Ebbers et al. |
| 11,167,125 B2 | 11/2021 | Moss et al. |
| 2004/0046938 A1 | 3/2004 | Gero |
| 2007/0083247 A1 * | 4/2007 | Wyeth ............... A61B 18/14 607/99 |
| 2008/0231337 A1 | 9/2008 | Krishnaswamy et al. |
| 2008/0319440 A1 | 12/2008 | Richardson et al. |
| 2011/0092973 A1 | 4/2011 | Nuccitelli et al. |
| 2012/0029395 A1 | 2/2012 | Sanai |
| 2012/0116266 A1 | 5/2012 | Houser et al. |
| 2012/0259323 A1 | 10/2012 | Manwaring et al. |
| 2013/0023871 A1 | 1/2013 | Collins |
| 2014/0364797 A1 | 12/2014 | Schoenbach et al. |
| 2015/0201991 A1 | 7/2015 | Zemlin |
| 2016/0278840 A1 * | 9/2016 | Kane ............... A61B 18/1482 |
| 2017/0203118 A1 | 7/2017 | Chang |
| 2017/0245928 A1 | 8/2017 | Xiao et al. |
| 2018/0078755 A1 | 3/2018 | Kreis et al. |
| 2019/0201089 A1 * | 7/2019 | Waldstreicher .... A61B 18/1492 |
| 2019/0269904 A1 * | 9/2019 | Kreis ............... A61N 1/36017 |

OTHER PUBLICATIONS

International Search Report and Written Opinion dated Dec. 21, 2021 for PCT/US2021/047879; 13 pages.

Nuccitelli et al.; Optimized nanosecond pulsed electric field therapy can cause murine malignant melanomas to self?destruct with a single treatment; International Journal of Cancer; 127(7); pp. 1727-1736; Oct. 1, 2010.

Wang et al.; Soiid-State High Voltage Nanosecond Pulse Generator; IEEE InPulsed Power Conference;pp. 1199-1202; 4 pages; Jun. 13, 2005.

* cited by examiner

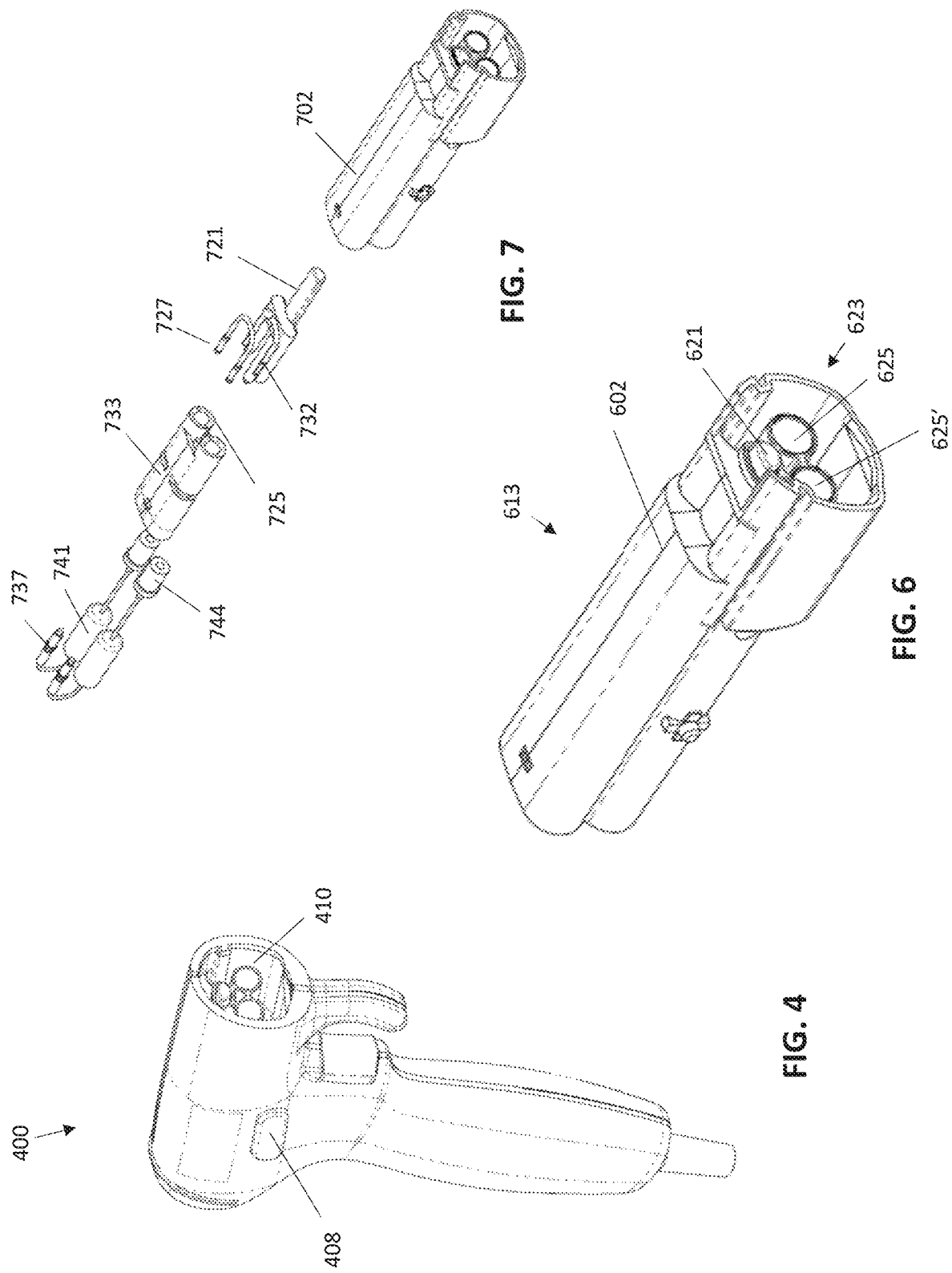

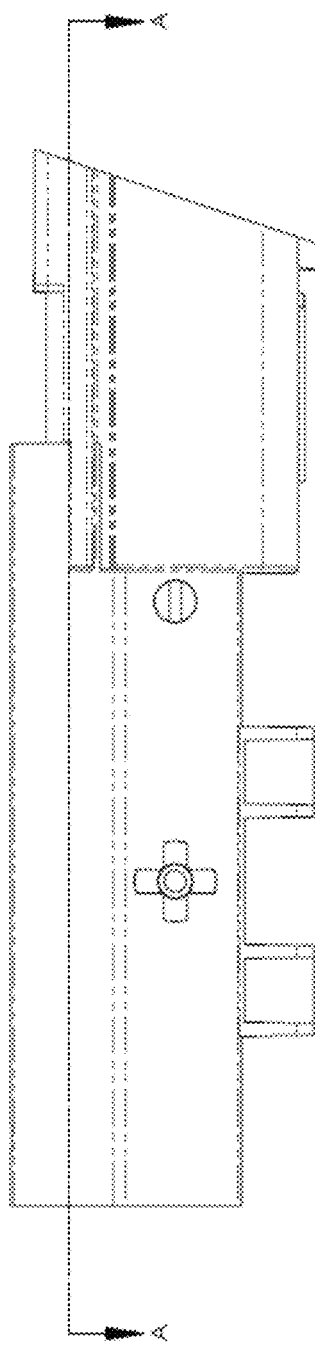
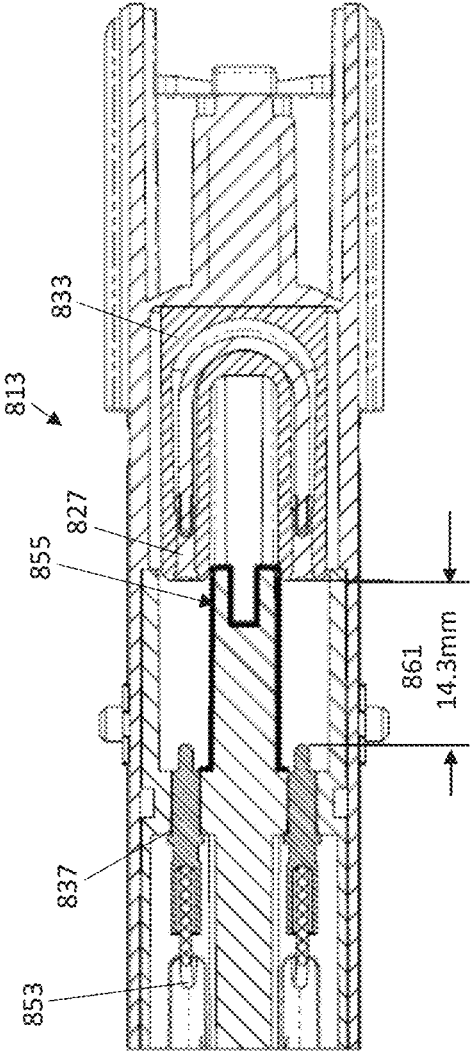
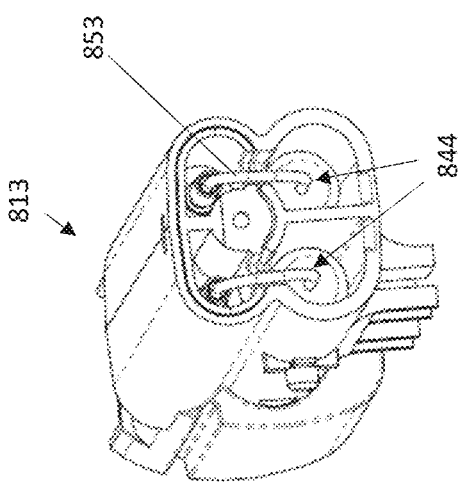
FIG. 8B
FIG. 8C
FIG. 8A

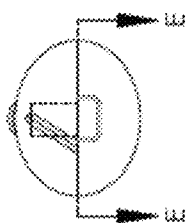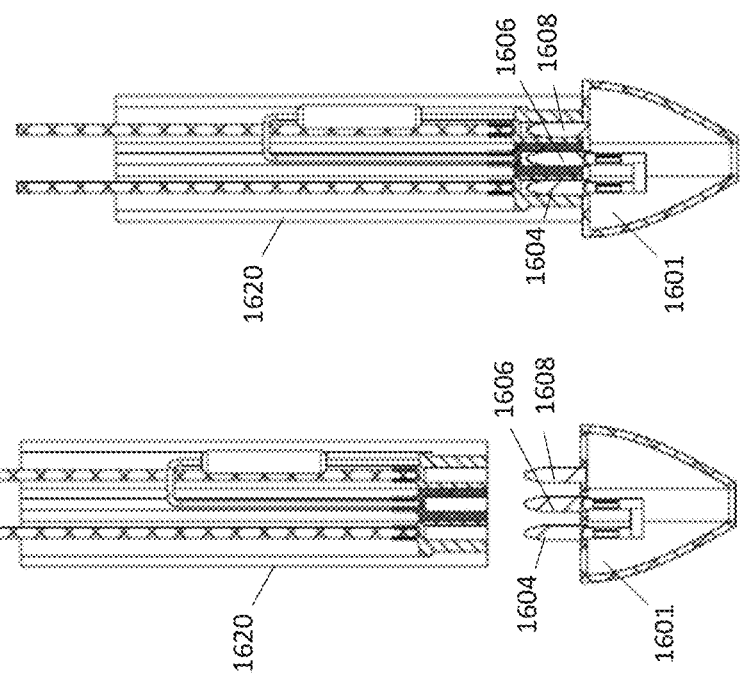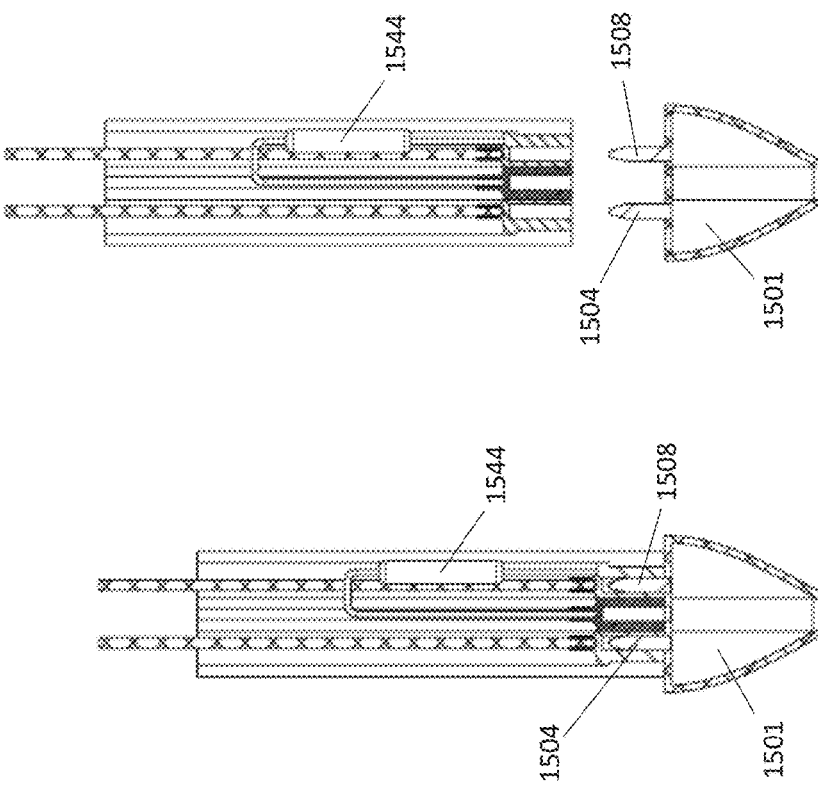

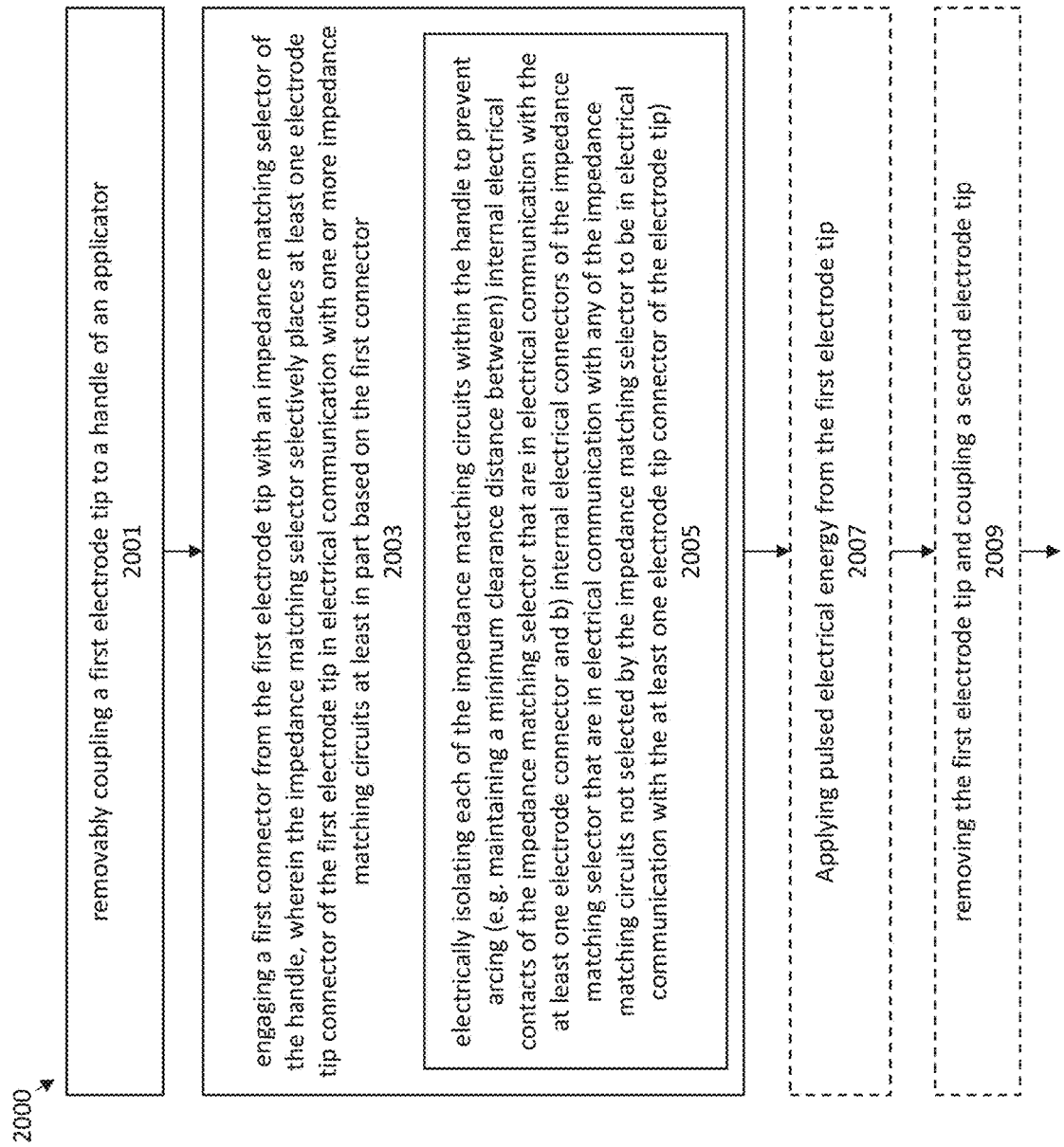

UNIVERSAL HANDPIECE FOR ELECTRICAL TREATMENT APPLICATOR

CROSS REFERENCE TO RELATED APPLICATIONS

This patent application is a continuation of International Application No. PCT/US2021/047879, filed on Aug. 27, 2021, titled "UNIVERSAL HANDPIECE FOR ELECTRICAL TREATMENT APPLICATOR," which claims priority to U.S. Provisional Patent Application No. 63/073,907, filed on Sep. 2, 2020, titled "UNIVERSAL HANDPIECE FOR ELECTRICAL TREATMENT APPLICATOR," each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are electrical treatment applicators, including handles that allow connection to a variety of removable electrode tips with selectable impedance matching. Specifically, described herein are handles/handpieces that select impedance matching based on an encoding shape engagement with a removable electrode tip, for high-voltage electrical therapy.

BACKGROUND

When applying rapid pulsing, poor impedance matching may lead to reflections and distortions in the applied electrical pulses. This problem may be particular acute when applying short (e.g., sub-microsecond) pulses at very high field strength, as have been described for electromanipulation of biological cells. For example, electric pulses may be used in treatment of human cells and tissue including tumor cells, such as basal cell carcinoma, squamous cell carcinoma, and melanoma. The voltage induced across a cell membrane may depend on the pulse length and pulse amplitude. Pulses shorter than about 1 microsecond may affect the cell interior without adversely or permanently affecting the outer cell membrane, and result in a delayed cell death with intact cell membranes. Such shorter pulses with a field strength varying in the range of several kV/cm to 100 kV/cm may trigger apoptosis (i.e. programmed cell death) in some or all of the cells exposed to the described field strength and pulse duration. These higher electric field strengths and shorter electric pulses may be useful in manipulating intracellular structures, such as nuclei and mitochondria.

Nanosecond high voltage pulse generators have been proposed for biological and medical applications. For example, see: Gundersen et al. "Nanosecond Pulse Generator Using a Fast Recovery Diode", IEEE 26th Power Modulator Conference, 2004, pages 603-606; Tang et al. "Solid-State High Voltage Nanosecond Pulse Generator," IEEE Pulsed Power Conference, 2005, pages 1199-1202; Yampolsky et al., "Repetitive Power Pulse Generator With Fast Rising Pulse", U.S. Pat. No. 6,831,377; Schoenbach et al. "Method and Apparatus for Intracellular Electro-Manipulation", U.S. Pat. No. 6,326,177; Kuthi et al., "High Voltage Nanosecond Pulse Generator Using Fast Recovery Diodes for Cell Electro-Manipulation", U.S. Pat. No. 7,767,433; Krishnaswamy et al., "Compact Subnanosecond High Voltage Pulse Generation System for Cell Electro-Manipulation", U.S. Patent Application No. 2008/0231337; and Xiao et al. "High-Voltage Analog Circuit Pulser with Feedback Control", U.S. Pat. No. 10,548,665 B2. The entire content of these publications is incorporated herein by reference.

Such pulse generators are used with various treatment applicators containing a set of electrodes. In some cases, an applicator may be configured to operate with multiple different types of electrodes (e.g., applicator tips) for use with a variety of different tissues or tissue geometries and/or therapies. However, the physical size of circuit components needed at the high voltages and currents make it difficult to provide an acceptable applicator configuration that can be used with a variety of differently configured removable/swappable electrode tips. It is desirable to provide improved treatment applicator configurations that will allow for impedance matching to reduce reflections and distortions in the applied electrical pulses and allow to use a variety of removable/swappable electrode tips with the same treatment applicator.

The methods and apparatuses described and illustrated herein may address the issues discussed above.

SUMMARY OF THE DISCLOSURE

Described herein are methods and apparatuses (e.g., devices and systems, including handles or handpiece for electric treatment applicators) for the automatically and/or mechanically (including electro-mechanically) selecting and applying impedance matching for a variety of differently configured treatment tips (electrode tips). Impedance matching of applied electrical energy, particularly energy applied to a biological tissue to be treated, may minimize reflections and may improve the power transferred. These methods and apparatuses may be useful for applying therapeutic energy, including but not limited to short, high field strength electric pulses, while avoiding the risk of arcing or otherwise harming the tissue. Further, these apparatuses and methods may be well suited, for example, for any treatments involving sub-microsecond (e.g., nanosecond, picosecond, etc.) pulsing, such as but not limited to the treatment of various diseases, skin disorders, and abnormal tissue growth.

In particular, the apparatuses and methods described herein may be configured for use with a plurality of differently configured treatment tips (e.g., single-use treatment tips or reusable), as will be described in greater detail herein.

The apparatuses described herein may be used with a pulse generator and may be provided as a part of the pulse generator systems. In particular, these apparatuses may include an applicator comprising a handle (also referred to as a handpiece or an applicator handle) that is configured to removably couple with a variety of different treatment tips (e.g., electrode tips), so that the applicator may deliver energy generated by the pulse generator through a treatment tip into the tissue. For clarity and avoidance of any doubt, the term "handle", "applicator handle" or "handpiece", as used herein, refers to any structure to support, hold or attach to the electrode portion (treatment tip portion) of the device, whether it is intended to be hand-held, or attached to the robotic arm, or for percutaneous or other minimally invasive applications and for catheter-based delivery. In some examples the handle may include a manual grip, in some examples it may be configured to be held by a robotic manipulator (e.g., arm, etc.), or it may be configured for introduction through the scope or a catheter. Typically, these apparatuses (e.g., device, instruments and systems, including handles) may engage with an electrode tip so that coupling and engaging the electrode tip with the handle automatically couples an appropriate impedance matching circuit within the handle to the electrodes of the electrode tip, so that the electrical energy applied to the electrode tip is modified by the selected impedance matched circuit.

In some examples, these handles, which may also be referred to as applicator handles, may include an interface for removably engaging the electrode tip, and a plurality of different impedance matching circuits. These impedance matching circuits may include one or more resistors and may be configured in the circuit in parallel to the electrodes of the electrode tip and the pulse generator. An impedance matching circuit may include one or more combinations of the impedance matching element; different impedance matching circuits may share impedance matching elements (e.g., resistors, inductors, capacitors, etc.). Thus, different impedance matching circuits may share components that may be combined in differently to create different impedance matching circuits by forming different combinations of overlapping components. The handle may also include an impedance matching selector that is part of the interface between the handle and the treatment tip. The impedance matching selector may receive the encoding shape connector or encoding shape connection from the electrode tip and may couple or configure the appropriate one or more impedance matching circuits in the handle to the electrode tip based on the encoding shape connection.

For example, described herein are handles for treatment applicators that may be used with a variety of different electrode tips, and may automatically, and/or mechanically and/or electro-mechanically, adjust the impedance matching, for example, by selecting a particular impedance matching circuit (e.g., in some examples a combination of shared circuit components) associated with a particular tip configured for coupling with the handle of the applicator. A handle as described herein may include: a plurality of impedance matching circuits; a plurality of handle connectors (e.g., electrical or electro-mechanical) configured to engage with a plurality of electrode tip connectors (e.g., electrical or electro-mechanical) on an electrode tip so that a plurality of electrodes of the electrode tip are in electrical communication with the pulse generator; and an impedance matching selector configured to selectively couple the plurality of electrode tip connectors with one or more of the impedance matching circuits of the plurality of impedance matching circuits based on an encoding shape connection with the electrode tip.

The impedance matching selector may be configured to receive the encoding shape connection from the treatment tip (electrode tip) in order to connect one or more of the impedance matching circuits within the handle to the electrode tip.

The encoding shape connection (also referred to herein as a keyed connector, or an encoding shape connector) may be one or more: projection, protrusion, cavity, pin, bar, bump, ridge, etc. In general, as used herein an encoding shape connection refers to a shape, configuration or orientation that corresponds to an impedance setting on the handle. The encoding shape connection may specifically identify a particular impedance setting when engaged when the tip engages with the handle via the mechanical connection between the tip and the handle. In some examples the encoding shape connection may be a protrusion extending from the electrode tip into the handle (e.g., into the impedance matching selector. In some examples the encoding shape connection comprises a plurality of pins. The encoding shape connection may be all or part of the electrical connector(s) of the electrode tip that are in electrical communication with the one or more electrodes on the electrode tip. For example, in some examples the encoding shape connection may be formed, as least in part, by the plurality of electrode tip connectors on the treatment tip. In one example, the encoding shape connection of the electrode tip includes a plurality of pins extending from the electrode tip that are conductive and also form the electrode tip electrical connector(s).

The plurality of impedance matching circuits may be housed within the handle. For example, a handle housing may enclose all or part of the plurality of impedance matching circuits. The plurality of impedance matching circuits may each include a pair of connectors, referred to herein as internal connectors, that may form a part of the impedance matching selector and may selectively couple each impedance matching circuit to the electrode tip electrical connectors in order to provide impedance matching. For example, the plurality of impedance matching circuits may be arranged so that the impedance matching circuits may each be connected in parallel with one another.

At least one of the plurality of impedance matching circuits may comprise a resistor configured to be arranged in a circuit in parallel between two or more of the plurality of electrode tip electrical conductors. In some examples these resistors may be between 10 and 800 Ohms (e.g., between 100 and 500 Ohms, between 10 and 500 Ohms, between 100 and 400 Ohms, between 100 and 800 Ohms, between 150 and 350 Ohms, between 200 and 800 Ohms, etc.). Multiple resistors may be used.

The impedance matching selector may include a plurality of internal connectors that may be static (e.g., in a fixed position relative to each other) or all or some of them may be movable. For example, the impedance matching selector may include a plunger configured to be displaced by the encoding shape connection with the electrode tip. Displacing the plunger may move one or more internal connectors (e.g., one or more pairs of internal connectors) into contact with another internal connector to place one or more of the plurality of impedance matching circuits in electrical contact (and in some cases, in parallel with) the connection between the electrical connectors of the electrode tip and the pulse generator.

Any of the apparatuses and methods described herein may be configured so that, even when operating to generate a sub-microsecond, high-voltage pulsed electrical field (e.g., equal or greater than 1 kilovolts per centimeter (kV/cm), 5 kV/cm, 10 kV/cm, 20 kV/cm, 50 kV/cm, 100 kV/cm, 150 kV/cm, 300 kV/cm, 500 kV/cm, etc.), arcing within the handle is prevented between the internal electrical connectors coupled to the plurality of impedance matching circuits. For example, in some examples the impedance matching selector comprises a first set of internal electrical contacts that are separated from a second set of internal electrical contacts by an air gap, and wherein the first set of electrical contacts is in electrical communication with the pulse generator forming a first impedance matching circuit of the plurality of impedance matching circuits and the second set of internal electrical contacts is in electrical communication with a second impedance matching circuit of the plurality of impedance matching circuits. In any of these examples the internal electrical contacts of the first set of internal electrical contacts may be separated from each other by a minimum clearance distance. The minimum clearance distance may be the distance that is greater than a shortest distance or path that prevents an arc between two conductive parts measured along any surface of combination of surfaces of an insulting material, and/or a shortest path in the air between two conductive parts that prevents an arc. See, e.g., WO2018053539, herein incorporated by reference in its entirety. For example, the minimum clearance distance may be of about 20 mm or greater (e.g., 25 mm or greater, 30 mm or greater, 35 mm or greater, 40 mm or greater, 45 mm or greater, 48 mm or greater, 50 mm or greater, etc.), e.g., when delivering pulsing at about 15 kV. In examples in which the delivered pulses are less than 15 kV, the minimum clearance distance may be proportionally smaller (e.g., 10 mm or greater, 15 mm or greater, etc., where the pulses delivered have a peak of about 10 kV).

As mentioned, in some examples all or some of the internal electrical contacts of the impedance matching selector may be moved when engaging the encoding shape connection of the electrode tip to the impedance matching selector. For example, a second set of electrical contacts (that coupled to one or more of the impedance matching circuits in the handle) may be configured to be displaced by impedance matching selector to place the second impedance matching circuit in parallel with the first impedance matching circuit based on the selected encoding shape connection with the electrode tip.

As mentioned, the impedance matching selector may include or be part of the (e.g., electrical or electro-mechanical) connector(s) on the handle that engage with the electrode tip (e.g., electrical or electro-mechanical) connectors to place the electrodes of the electrode tip in communication with the pulse generator. In some examples, the plurality of handle connectors may form a part of the impedance matching selector.

For example, a handle of a treatment (e.g., pulse) applicator may include: a plurality of impedance matching circuits; a plurality of handle connectors configured to engage with a plurality of electrode tip connectors so that a plurality of electrodes of the electrode tip are in electrical communication with the pulse generator through one or more of the impedance matching circuits; and an impedance matching selector configured to selectively couple the plurality of electrode tip connectors with one or more of the impedance matching circuits of the plurality of impedance matching circuits based on an encoding shape connection with the electrode tip, wherein the impedance matching selector comprises a first set of internal electrical contacts that is separated from a second set of internal electrical contacts by an air gap, and wherein the first set of electrical contacts is in electrical communication with a pulse generator forming a first impedance matching circuit of the plurality of impedance matching circuits and the second set of internal electrical contacts is in electrical communication with a second impedance matching circuit of the plurality of impedance matching circuits. In some examples all or some of the impedance matching circuits may be on the tip and/or on the pulse generator rather than in the handle. In some examples the impedance matching components (e.g., resistors or other impedance circuit components) may be in both the handle and the tip and/or in the pulse generator.

These handles may be part of an instrument (e.g., an applicator) or a system that may include a pulse generator. Any of these instruments or systems may also or alternatively include one or more electrode tips. For example, an applicator may include: a removable electrode tip, the electrode tip comprising a plurality of electrodes, and a plurality of electrode tip connectors in communication with the plurality of electrodes; and a handle, the handle comprising a plurality of impedance matching circuits (which may be configured as dedicated circuits or may overlap and share components between difference circuits); a plurality of handle connectors configured to engage with the plurality of electrode tip connectors so that the plurality of electrodes of the electrode tip are in electrical communication with the pulse generator; and an impedance matching selector configured to selectively couple the plurality of electrode tip electro-mechanical connectors with one or more of the impedance matching circuits of the plurality of impedance matching circuits based on an encoding shape connection with the electrode tip.

The electrode tip may be configured to be removably coupled to a distal end of the handle. Any of these applicators or instruments may include additional electrode tips, such as a second removable electrode tip having an encoding shape connection that is different from the encoding shape connection of the removable electrode tip (e.g., the first removable electrode tip).

Also described herein are systems, including systems for mechanically selecting impedance matching for an electrode tip when coupling the tip to a handle of a pulse generator. For example, a system may include: a pulse generator; a removable electrode tip, the removable electrode tip comprising: a plurality of electrodes, and a plurality of electrode tip electrical connectors in communication with the plurality of electrodes; a handle, the handle comprising a plurality of handle electrical connectors configured to engage with the plurality of electrode tip electrical connectors so that the plurality of electrodes of the electrode tip are in electrical communication with the pulse generator; a plurality of impedance matching circuits; and an impedance matching selector configured to selectively couple the plurality of electrode tip electrical connectors with one or more of the impedance matching circuits of the plurality of impedance matching circuits based on an encoding shape connection with the electrode tip.

In any of the apparatuses (e.g., systems) described herein the impedance matching circuits may be located in the handle and/or the tip, and/or the pulse generator. The impedance matching circuits may be spread out between the tip, the handle and/or the pulse generator. In some examples, as described herein, the impedance matching circuits may be primarily or exclusively located in the handle. In some examples the impedance matching circuits may be primarily or exclusively located in the pulse generator.

Alternatively or additionally, in any of the examples described herein, the impedance matching circuits may share circuit components (e.g., resistors, capacitors, inductors, etc.) between some (or all) of the separate impedance matching circuits described herein.

As described above, in general the interface between a tip and the pulse generator, e.g., the handle, may determine which impedance matching circuits (and therefore which resistors and/or other elements of the impedance matching circuit) may be connected between the electrode(s) in the tip and the pulse generator. For example, the tip configuration, including tip size, and/or any other shape that may be matched (shape matched) to the handle may mechanically (and in some cases electrically) select the impedance matching circuit, or the components (e.g., resistors, capacitors, inductors, etc.) forming the impedance matching circuits.

As mentioned, the encoding shape connection of the electrode tip may comprise a protrusion extending from the electrode tip into the handle. For example, the encoding shape connection may comprise a plurality of pins forming the plurality of electrode tip connectors.

Also described herein are methods of using any of these apparatuses and systems. For example, described herein are methods of selecting an impedance circuit for a removable electrode tip of a pulse applicator that include: removably coupling a first electrode tip to a handle of a pulse applicator; and engaging a first encoding shape connector from the first electrode tip with an impedance matching selector of the handle, wherein the impedance matching connector selectively places a plurality of electrode tip connectors of the first electrode tip in electrical communication with one or more impedance matching circuits within the handle based at least in part on the first encoding shape connector, so that a pulse generator may be in electrical communication with the first electrode tip through the selected one or more impedance matching circuits. In some examples the method may include coupling the pulse generator to the tip. Alternatively or additionally, the tip may be connected to the handle (e.g., the handled of a pulse applicator) before connecting to the pulse generator. Thus, it is not necessary to couple the tip to the handle with the pulse generator attached. In general, the methods described herein, including methods of selecting an impedance circuit, may be for use with treating tissue and/or cells that are cultured (e.g., in vitro), in addition or instead of in vivo cells and/or tissue.

Engaging the first encoding shape connector may include displacing a plunger within the handle to connect a second impedance matching circuit parallel with a first impedance matching circuit. In some examples engaging the first encoding shape connector comprises inserting a plurality of pins forming the plurality of electrode tip connectors into the impedance matching selector so that the plurality of pins makes electrical contact with one or more internal electrical contacts coupled to one or more of the impedance matching circuits within the handle. In some examples the plurality of pins may make electrical contact with the one or more internal electrical contacts depending on a length of each of the pins of the plurality of pins.

Any of these methods may include applying pulsed electrical energy (e.g., high-voltage pulsed electrical energy, including nanosecond or shorter pulses) from the electrode tip.

The methods described herein may include removing the first electrode tip and coupling a second electrode tip (or additional electrode tips), wherein a second encoding shape connector from the second electrode tip, that is different from the first encoding shape connector, engages with the impedance matching selector of the handle to selectively place the second electrode tip in electrical communication with a different one or more impedance matching circuits than the one or more impedance matching circuits in electrical communication with the plurality of electrode tip electrical connectors of the first electrode tip.

In general, the methods described herein may include electrically isolating each of the impedance matching circuits within the handle to prevent arcing by maintaining a minimum clearance distance or separating gap (e.g., an air gap or fluid gap) between internal electrical contacts of the impedance matching selector that are in electrical communication with the plurality of electrode tip electrical connectors and internal electrical connectors of the impedance matching selector that are in electrically communication with any of the impedance matching circuits not selected by the impedance matching selector to be in electrical communication with the plurality of electrode tip connectors of the electrode tip. These methods may include maintaining the separating minimum clearance distance, including maintaining a minimum path length (along any connecting surfaces and/or through the air) between the internal electrical contacts of the impedance matching selector that are in electrical communication with the plurality of electrode tip connectors and internal electrical connectors of the impedance matching selector that are in electrically communication with any of the impedance matching circuits not selected by the impedance matching selector to be in electrical communication with the plurality of electrode tip connectors of the electrode tip. The minimum clearance distance may be, for example, about 30 mm or greater (e.g., 35 mm or greater, 40 mm of greater, 45 mm or greater, 50 mm or greater, etc.).

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 4 is another example of a handle of the treatment applicator as described herein.

FIG. 6 shows one example of an impedance matching selector of a handle as described herein.

FIG. 7 is a partially exploded view of components of an impedance matching selector of a handle as described herein.

FIG. 8A is a cut-away back view of a portion of an impedance matching selector of a handle as described herein.

FIG. 8B shows a perspective view of a portion of a handle including an impedance matching selector.

FIG. 8C is an example of a top sectional view through the impedance matching selector shown in FIG. 8B.

FIG. 13B shows an example in which the encoding shape connection comprises two short pins and the impedance matching selector is configured so that the second set of internal connectors are not coupled to the short pin and, therefore, to the electrode tip connectors.

FIG. 15A shows an end view of an electrode tip and handle portion.

FIGS. 15B-15C show top cross sectional and cut away views (through line J-J) of the example shown in FIG. 15A, of an electrode tip coupled to an impedance matching selector portion of a handle as described herein.

FIG. 16A shows an end view of another example of an electrode tip and handle portion.

FIGS. 16B-16C both illustrate an example of a cross section of an electrode tip coupling to an impedance matching selector portion of a handle. In FIG. 16B the electrode tip is connected and in FIG. 16C the electrode tip is removed.

FIG. 20 schematically illustrates one example of a method of selecting an impedance circuit as described herein.

DETAILED DESCRIPTION

The methods and apparatuses described herein generally relate to electrical treatment applicators (e.g., handles or handpieces) that may be used with a plurality of different electrode tips each having different configurations. A handle of the treatment applicator may automatically set the impedance matching for the electrodes of the electrode tip. In general, the handle of the applicator may include a plurality of different impedance matching circuits that may be selectively coupled to the electrodes of the electrode tip based on the engagement of the electrode tip and the handle of the applicator. The handle may include an impedance matching selector that may engage each electrode tip and, based on the manner in which the electrode tip engages with the impedance matching selector, the handle is configured to put one or more of the impedance matching circuits in electrical communication with the electrodes of the electrode tip. The impedance matching circuits may be formed of different impedance matching circuit components (e.g., resistors, capacitors, inductors, etc.) that may be shared by more than one of the impedance matching circuits. For example, coupling the tip to the handle may connect impedance matching components into a particular impedance matching circuit. Thus, although the handle (or any other appropriate portion of the apparatus, such as the tip and/or pulse generator) may include a plurality of impedance matching circuits, these circuits may be assembled or connected in contact with the one or more tips; it is understood that these incomplete or unconnected impedance matching circuits, which are completed by connection of a particular tip type to the handle, are still referred to herein as impedance matching circuits.

The impedance matching selectors described herein may also generally be configured so that they may be operated safely and accurately with pulse generators that provide high voltage, sub-microsecond (e.g., nanosecond) pulsing. For example, the impedance matching selectors described herein may be configured to prevent arcing within the handle by including standoff spacing, e.g., between internal connectors connecting one or more of the impedance matching circuits, and minimum clearance distance that is greater than a minimum safe distance, such as about 20 mm or greater, about 25 mm or greater, about 30 mm or greater, about 35 mm or greater, about 40 mm or greater, about 45 mm or greater, etc. (e.g., when delivering pulsing at about 15 kV). In examples in which the delivered pulses are less than 15 kV, the minimum clearance distance may be proportionally smaller (e.g., where the pulses delivered have a peak of about 10 kV, the minimum clearance distance may be 10 mm or greater, 15 mm or greater, etc.).

Figure 1A:
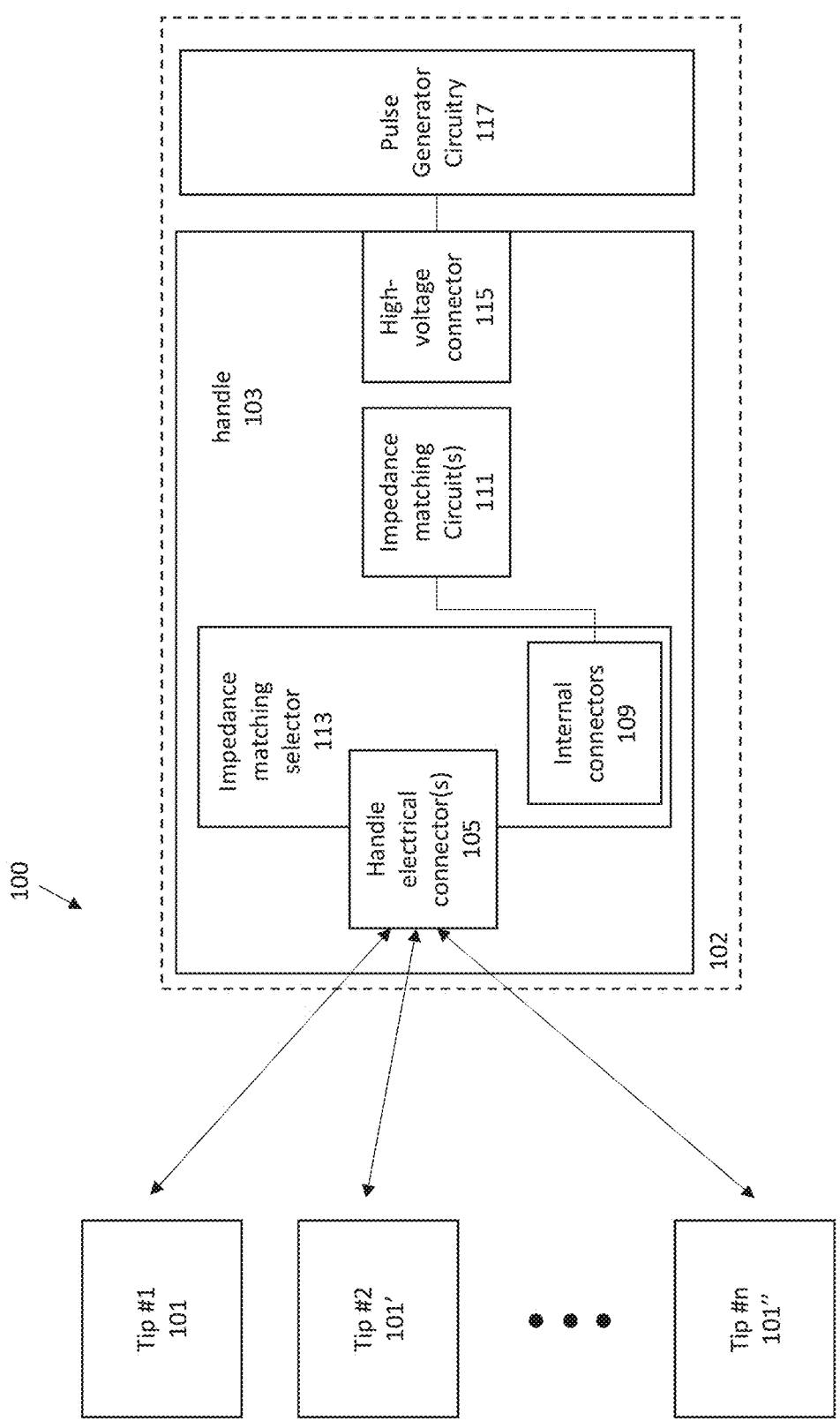
FIG. 1A schematically illustrates one example of an apparatus as described herein, including a handle that is configured to select an impedance matching circuit based on an encoding shape connection with an electrode tip.

FIG. 1A schematically illustrates one example of an apparatus 100 as described herein, shown as a system including a plurality of n electrode tips (101, 101' . . . 101") that may couple with an applicator handle 103 of an applicator 102. The handle 103 may include an impedance matching selector 113 that may include a plurality of internal connectors 109. The electrode tips may each couple to the handle both electrically and mechanically, so that the electrode tip may be held at an end of the handle for application of electrical energy to a target tissue. The electrode tip may electrically couple to the handle through one or more handle connectors, for example, electrical or electro-mechanical connectors 105. The handle connectors may be part of the impedance matching selector 113 or they may be separate from the impedance matching selector. For example, the handle connectors may be configured as electrical contacts (e.g., external electrical contacts), with which one or more electrode tip connectors may mate. The handle connectors may be male and/or female connectors. For example, the handle connectors may include female electrical contacts that receive input from a male (e.g., pin) electrical contact of the electrode tip.

The impedance matching selector may connect to one or more of a plurality of impedance matching circuits 111 within the handle 103, so that the impedance matching selector may selectively engage one or more individual or combinations of the impedance matching circuit components, typically connected electrically in parallel with the connection between the handle electrical connector(s) 105 and the pulse generator circuitry 117, to adjust impedance matching of the electrode tip based on the way that the electrode tip engages with the impedance matching selector. For example, the electrode tip may engage with the impedance matching selector through the handle connector; in some examples the electrode tip connectors include one or more pins that extend from the electrode tip into the handle connector. In this example, the handle connector forms a part of the impedance matching selector, and the one or more pins of the electrode tip connectors may engage with one or more sets of internal connectors 109 within the impedance matching selector to include one or more of the impedance matching circuits. In this example the connection between each of the different electrode tips may be differently keyed (e.g., shape-matched) to the impedance matching selector based, for example, on the size/shape (e.g., length), and/or in some examples number, of pins forming the plurality of electrode tip connectors.

Impedance matching components may be shared between one or more impedance matching circuit, as described herein. Impedance matching components may include resistors, including variable resistors, e.g., potentiometers (which may be configured for variable impedance matching). In some examples the tip, including an encoding shape connector, may engage a variable resistor and drive it to different values. Thus, in some examples the handle may include one or more variable impedance matching components, such as resistors, that may be set or adjusted automatically and, in some examples. mechanically, e.g., by engaging an encoding shape connector between the tip and the handle, when the tip engages with the handle.

Alternatively or additionally, in some examples the connection between the electrode tip and the handle (e.g., the impedance matching selector) may be through a protrusion extending from the electrode tip into the handle. The protrusion may be referred to as an encoding shape (e.g., keying) protrusion, and may be separate from the electrode tip electrical connectors or it may be part of the electrode tip electrical connectors. For example, the encoding shape protrusion may extend from the electrode tip and may engage with a mechanism on the impedance matching selector when the electrode tip is connected to the handle; the encoding shape protrusion may (or may not) displace a member (e.g., a plunger, slider, cam, etc.) of the impedance matching selector which may in turn displace one or more internal connectors of the impedance matching selector to place one or more impedance matching circuit element combinations 111 in communication, typically in parallel, with the connection between the electrode tip electrical connectors connected to the handle electrical connectors and the pulse generator circuitry 117. In this manner, the impedance matching selector may set the impedance matching circuit for the electrode tip based on the encoding shape connection with the electrode tip.

As shown in FIG. 1A, in some examples the handle 103 may be part of a treatment applicator for use with a pulse generator that is configured to deliver sub-microsecond (e.g., nanosecond) pulsed electric fields (e.g., generating a high peak voltage, such as 2 kilovolts per centimeter (kV/cm) or greater, e.g., between 5 kV/cm and 500 kV/cm, between 10 kV/cm to 100 kV/cm, greater than 20 kV/cm, greater than 50 kV/cm, greater than 100 kV/cm, etc.). The pulse generator may generate pulses at a frequency ranging from 0.1 per second (Hz) to 10,000 Hz, for example. Thus, in some examples the applicator handle may include a high voltage connector 115 for coupling the applicator 102 to the rest of the pulse generator circuitry 117 that is configured to generate the pulses.

Thus, the apparatuses described herein may be configured for the delivery of nanosecond pulsed electric fields (sub-microsecond pulsed electric fields), which may include an electric field with a sub-microsecond pulse width of between 0.1 nanoseconds (ns) and 1000 nanoseconds, or shorter, for example, 1 picosecond. As mentioned, these pulses may have a high peak voltage, such as about 5 kilovolts per centimeter (kV/cm), 20 kV/cm to 500 kV/cm, etc. Treatment of biological cells with such apparatuses may use a multitude of periodic pulses at a frequency ranging from 0.1 per second (Hz) to 10,000 Hz. However, although the apparatuses described may be adapted for, and particularly well suited for, the delivery of therapeutic sub-microsecond pulses, they may also be used as electrodes to deliver other therapeutic treatments, including treatments with continuous (non-pulsed) energy, and treatments using slower than nanosecond pulses (e.g., microsecond, millisecond, or longer duration pulses).

The apparatuses described herein may be used to deliver one or more pulsed electrical treatments to treat various disorders and disease, including but not limited to cancer, such as the treatment of cancerous tumor cells. These apparatuses and methods may also or alternatively be used to selectively and specifically drive tumor cells to undergo apoptosis, a programmed cell death, causing tumors to shrink to nonexistence after treatment. A subject's immune system may be stimulated to attack all similar tumor cells, including those of tumors that are not within the treated tumor. In general, a disease may include any abnormal condition in or on a subject that is associated with abnormal, or uncontrolled growths of tissue, including those that are cancerous, precancerous, and benign, or other diseases as known in the art. Apoptosis of a tumor or cell includes an orderly, programmed cell death, or as otherwise known in the art.

As used herein, a "tumor" includes any neoplasm or abnormal, unwanted growth of tissue on or within a subject, or as otherwise known in the art. A tumor can include a collection of one or more cells exhibiting abnormal growth. There are many types of tumors. A malignant tumor is cancerous, a pre-malignant tumor is precancerous, and a benign tumor is noncancerous. Examples of tumors include a benign prostatic hyperplasia (BPH), uterine fibroid, pancreatic carcinoma, liver carcinoma, kidney carcinoma, colon carcinoma, pre-basal cell carcinoma, and tissue associated with Barrett's esophagus.

In general, any of the systems described herein may include a pulse generator. In some examples the treatment applicators of the present disclosure may include one or more electrode tips. These tips may include one or more type of electrodes, such as needle electrodes, plate electrodes, surface (e.g., flat) electrodes, etc. The electrode tips described herein may be disposable and may be configured for a single or limited use (e.g., single use, single session use, etc.). The electrode tips may be configured to connect or couple (both electrically and/or mechanically) to a reusable applicator device, such as a handle that may be connected to a control system including a pulse generator, as described above. The control system may control delivery of electrical pulses through the electrode tip. These apparatuses may be particularly well adapted for delivery of high-energy (high voltage) pulse lengths, for example, of between 1 and 990 nanoseconds, including pulse lengths of between 50 and 300 nanoseconds, or about 100 nanoseconds.

For example, a pulse generator system may include any of the electrode tips described herein ("electrodes"), a user control input (e.g., footswitch) and user interface (display, monitor, speaker, etc.). The user control input and interface may be connected to the control circuitry within a housing that holds the electronic components. The electrode tips may be connected to the applicator (e.g., handle) and the handle may be connected to the other pulse generator circuitry/ electronic components through a high voltage connector 115, as mentioned above. Examples of such high voltage connectors are described in the co-pending and co-owned International patent application PCT/US2017/052340, which is herein incorporated by reference in its entirety. The user may input or select treatment parameters, such as a number of pulses, amplitude, pulse duration, and frequency information, via one or more input devices, such as a numeric keypad, touch screen, mice, track pad, stylus, pen, speaker, etc.

Figure 1B:
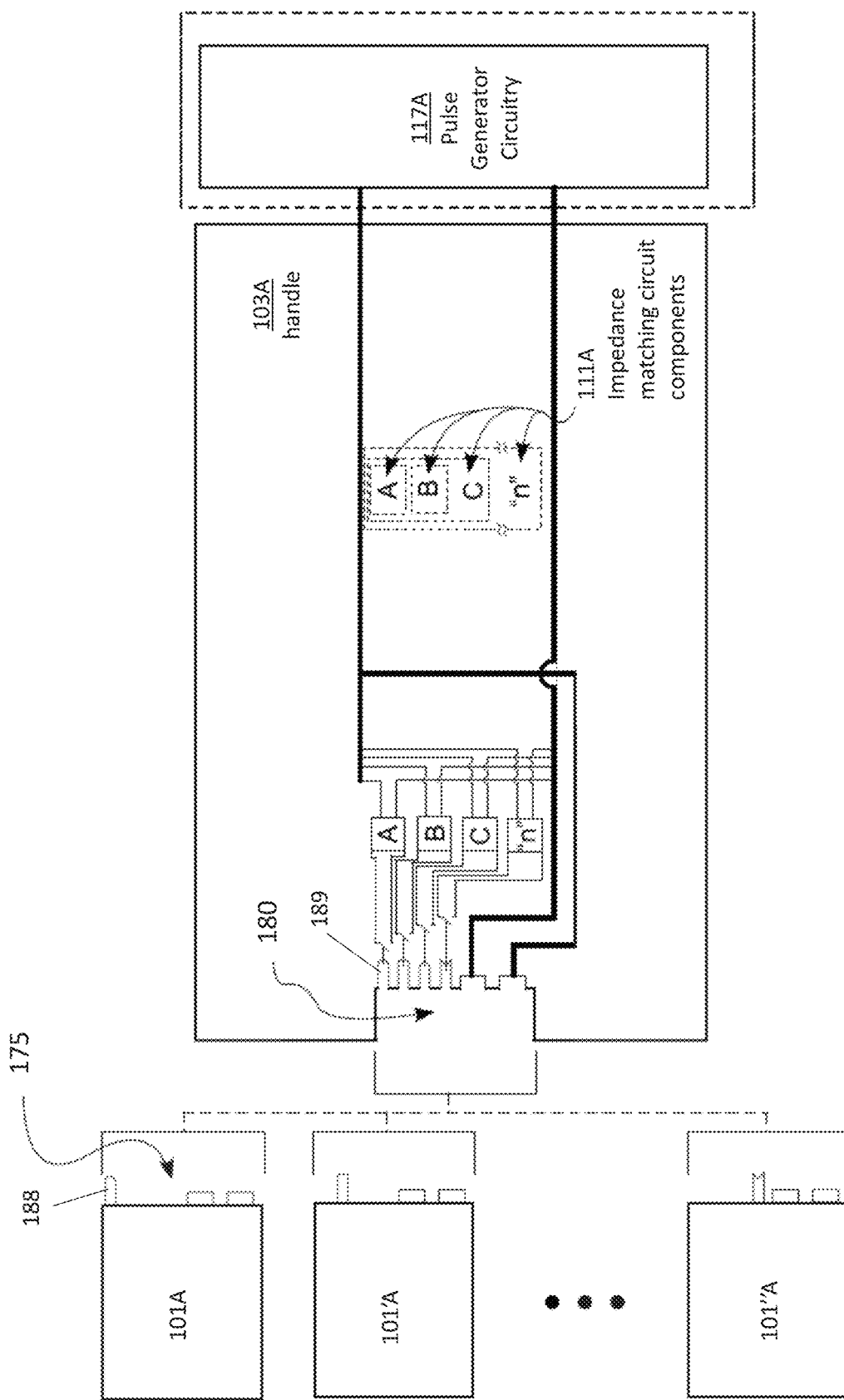
FIG. 1B schematically illustrates another example of an apparatus as described herein, including a handle having an electro-mechanical tip to handle connector that is configured to select an impedance matching circuit based on a configuration of an electrode tip.

FIG. 1B schematically illustrates an example of a handpiece, which may be referred to as a universal handle or unified handpiece, for use with multiple electrode tips as described herein. In FIG. 1B a plurality of n electrode tips (101A, 101'A . . . 101"A) are shown. Each electrode tip in this example has a connector to connect the tip to the handle so that the shape matched connector between the handle and the tip; the handle is configured so that it can receive and removably secure to a variety of different types of tips. Thus, the handle may be referred to as a universal applicator handle 103A, which may connect or be connected to pulse generator circuitry 117A. The handle 103A may include a receiving connector 180 (e.g., tip receiving connector) that is configured to receive a variety of different types of tips, e.g., having different encoding shapes. Upon engagement of the tip to the handle connector, the encoding shape of the tip 175 may engage with the handle and couple the tip (e.g., one or more electrodes) with one of a plurality impedance matching circuits in the handle. In some examples the connection between the tip and the receiving connector in the handle may engage with the encoding selector in the handle to complete a particular corresponding impedance matching circuit. As mentioned above, in some examples the impedance matching circuits within the handle (and/or in the tip and/or in the pulse generator circuitry) may share one or more impedance matching components 111A. In FIG. 1B, impedance matching circuits may be selected and/or completed by combinations of A, B, C . . . n. In some examples, an electrode tips may not require impedance matching; in this case, the tip may not (when connected) not require selection of an additional impedance matching circuit (or elements forming the impedance matching circuit). In some examples impedance matching may include connecting (for some tips) impedance matching circuits in parallel. In some cases, where impedance matching is not required, no parallel circuit path is created.

As shown in FIG. 1B, when a treatment tip, such as 101A, is connected to handle 103A, there may be a specifically configured mechanical connection, which may be referred to herein as an encoding shape connector (shown by example in FIG. 1B as a round-ended pin 188 extending to the right near the top of the handle) that is configured as a mechanical feature of the tip (on the facing connector of the tip) that may engage with a handle 103A in a receiving connector 180 (shown in this example as a cylindrical, round-bottomed opening 189 in the upper portion of the handle receiving connector), such that engagement of tip #1, 101A, into the receiving connector of the handle causes a connection (illustrated as a latching switch in FIG. 1B) to be made to a first impedance-matching circuit, which may include a combination of impedance matching circuit components ("A"), thus placing this first impedance matching circuit ("A") in parallel with the electrodes in the tip (not shown in FIG. 1B) that are adapted to contact the tissue to be treated. Similarly, when a different treatment tip such as 101'A is connected to handle 103A a different encoding shape connection (shown in FIG. 1B as a square ended post extending slightly offset from the upper right top of the handle-engaging side of the tip) which may mate with a complementarily receiving feature in the receiving connector 180 of the handle 103A (shown as a cylindrical square-bottomed hole); this connection may engage a second impedance-matching circuit ("B"), which may be separate from circuit "A" or may include some or all of these components (e.g., connect in parallel and/or in series), in addition to additional components. In this example, the electrodes on the second tip 101'A may therefore be electrically connected in parallel with the impedance matching circuit ("B"). Similarly, when other treatment tips, such as 101"A (or any number of additional different tips) are connected to the handle 103A different encoding shape connections on each of these different types of tips may make specific mechanical connections with the handle 103A. Typically, each of these different tip types may have one or more different electrode properties, such as different sizes of electrodes, different number of electrodes, different electrode spacing, different electrode materials, different electrode lengths, different electrode widths, etc., which may require different impedance matching, as described herein.

Figure 1C:
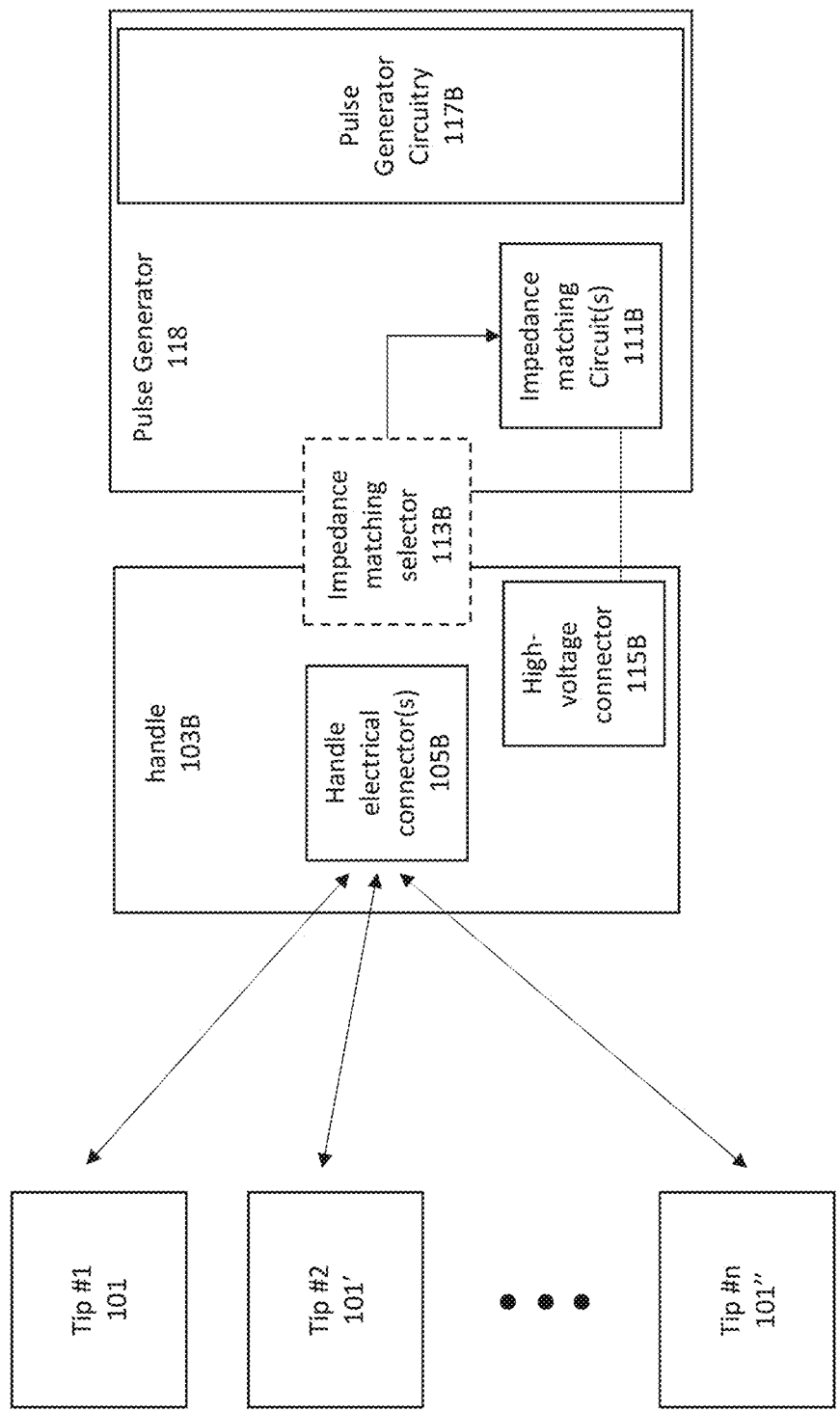
FIG. 1C schematically illustrates an example of an apparatus as described herein, including an impedance matching circuit that is present within the pulse generator.

In general, as mentioned above, the impedance matching circuit(s) may be included as part of (or distributed between) the tip, handle and/or the pulse generator. FIG. 1C schematically illustrates an example in which the impedance matching circuit(s) 111B is/are within the pulse generator 118 portion of the system. An impedance matching selector 113B may be part of either the handle 103B or the pulse generator 118, or distributed between both. The impedance matching selector 113B may include a plurality of internal connectors that may connect, directly or indirectly, with the electrode tips; as described herein, the electrode tips may each couple to the handle both electrically and mechanically, so that the electrode tip may be held at an end of the handle for application of electrical energy to a target tissue. The electrode tip may electrically couple to the handle through one or more handle connectors, for example, electrical or electro-mechanical connectors. The handle connectors (e.g., handle electrical connectors 105B) may be part of the impedance matching selector 113B or they may be separate from the impedance matching selector. For example, the handle connectors may be configured as electrical contacts (e.g., external electrical contacts), with which one or more electrode tip connectors may mate. In FIG. 1C, the system may include a plurality of n electrode tips (101, 101' . . . 101") that may couple with a handle 103B of an applicator. The handle connectors may be male and/or female connectors. For example, the handle connectors may include female electrical contacts that receive input from a male (e.g., pin) electrical contact of the electrode tip. The handle 103B may electrically connect to the pulse generator through a high voltage connector 115B. The impedance matching circuit(s) 111B may be between the high voltage connector and the pulse generator circuitry 117B.

The impedance matching selector 113B may connect to one or more of a plurality of impedance matching circuits 111B within the pulse generator so that the impedance matching selector may selectively engage one or more individual or combinations of the impedance matching circuit components, e.g., in parallel with the connection between the handle electrical connector(s) 105B and the pulse generator circuitry 117B, to adjust impedance matching of the electrode tip based on the way that the electrode tip engages with the handle and directly or indirectly with the impedance matching selector 113B. For example, the electrode tip may engage with the handle, which may detect (either mechanically or electrically) an impedance setting specific to a particular tip. The impedance matching selector 113B may detect the impedance setting directly or indirectly. In one example the electrode tip connectors may include one or more pins that extend from the electrode tip into the handle connector and displace corresponding pins in the handle which can them be detected by the impedance matching selector in the pulse generator; the one or more pins of the electrode tip connectors may indirectly engage with one or more sets of internal connectors (e.g., 109) within the impedance matching selector and this may in turn engage one or more of the impedance matching circuits 111B in the pulse generator. Thus, the connection between each of the different electrode tips may be differently keyed (e.g., shape-matched) and this different keying may be transmitted to the impedance matching selector. Alternatively in some examples the impedance matching selector may include software or firmware for encoding (e.g., electrically encoding) the impedance setting corresponding to a particular tip and may transfer the encoded impedance setting to the impedance matching circuit 111B in the handle.

In some examples the impedance matching circuit(s) 111B may be entirely or partially included in each tip. For example each type of tip having a different corresponding impedance setting may include a particular impedance matching circuit that is electrically connected to the handle electrical connector(s) and any high voltage connector coupling the handle to the pulse generator.

Figure 2:
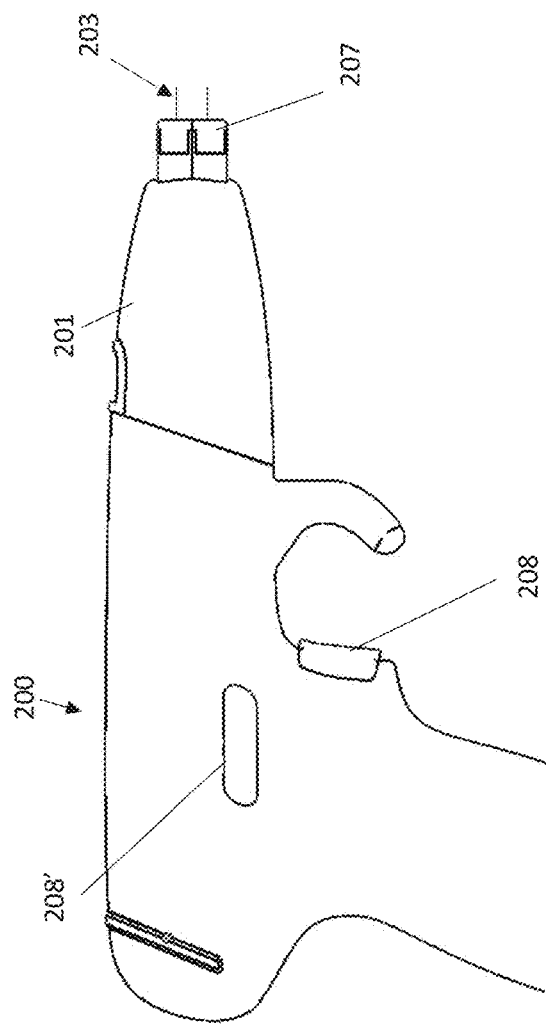
FIG. 2 shows one example of a handle of a treatment applicator engaged with one example of an electrode tip.

FIG. 2 illustrates one example of an applicator handle 200 as described herein. In this example, the reusable handle (also referred to herein as an applicator handle or universal handle) may be configured as a pistol grip-shaped body that couples to an electrode tip 201, as shown. The electrode tip 201 in this example includes a plurality of penetrating (e.g., needle) electrodes 203. The electrode tip may include an insulating, distal-facing portion 207 that may be soft and/or compliant. The reusable handle 200 may include one or more controls 208, 208' that may be used to control the delivery of electrical energy through the electrodes.

Figure 3:
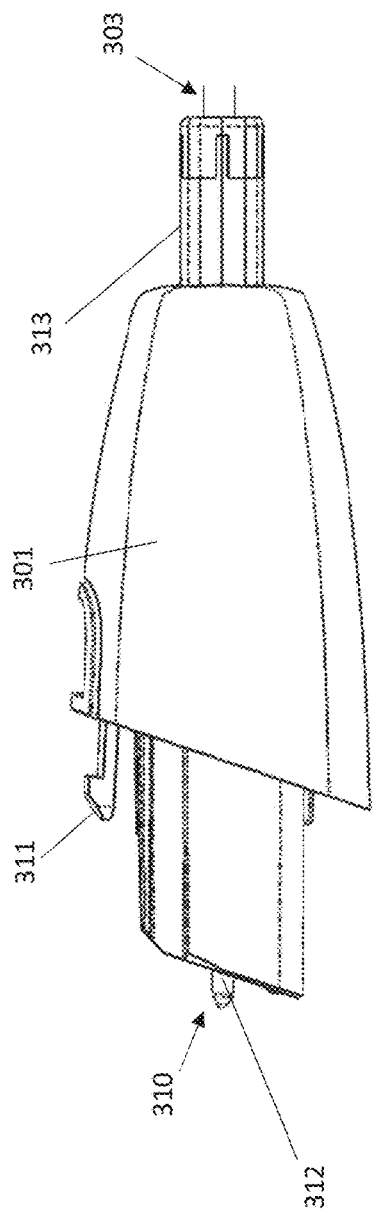
FIG. 3 shows one example of an electrode tip as described herein.

In general, the electrode tip 201 may engage with an applicator handle 200 in an interface region that allows the tip to removably electrically and mechanically couple with the handle. FIG. 3 illustrates one example of an electrode tip that may be used to (and for which an impedance matching selector in the applicator handle may automatically and mechanically) set (e.g., select) the impedance matching of the electrode tip from a plurality of pre-set impedance matching circuits within the handle of the apparatus.

In FIG. 3, the electrode tip is generally elongate (extending proximally to distally) and includes a treatment tip housing 301, having a slightly elongated, tapered shape. An electrode partition (configured in this example as a housing) 313 extends from the distal end of the treatment tip housing. A mechanical connector on the proximal end 310 may couple with the handle and may also include one or more electrical connectors 312 for coupling with the electrodes 303, which may extend from the electrode tip housing (or alternatively, may be extendable from within the electrode housing). The distal-facing (e.g., tissue facing) end of the electrode housing 313 may be covered by an insulating cover. A plurality of treatment needle electrodes 303 are shown projecting from the electrode housing. In this example the electrodes are needle electrodes that may have a sharp and beveled distal end but are cylindrical needles. However, the needle electrodes are shown as an example only, and any type and shape of electrode may be used, for example, various types of non-penetrating electrodes (e.g., blunt pins, wire electrodes, surface electrodes, etc.). The electrodes may be insulated or un-insulated; in some examples the treatment electrodes are insulated along a portion of their length, but the distal end (e.g., the distal 0.5 mm, 1 mm, 1.2 mm, 1.5 mm, 1.7 mm, 2 mm, etc.) are un-insulated. The electrode tip may include a mechanical connector 311 (shown by example as a snap or latch) that couples the tip to the handle. As mentioned above, in some examples this mechanical connector and/or the electrical connector(s) 312 may form at least a part of the connection to the handle that may engage with all, none or a part of the impedance matching selector.

FIG. 4 illustrates an example of an applicator handle 400 that is configured to receive and engage, both mechanically and electrically, a variety of different electrode tips. In this example, similar to FIG. 2, the handle includes multiple controls, such as controls 408, that may be used to control the application of the therapy (e.g., the electrical energy). The handle may also include a receiving opening 410 for receiving an electrode tip (not shown). The receiving opening may include a portion of the impedance matching selector that receives an encoding shape connector such as a protrusion, etc.

Figure 5A:
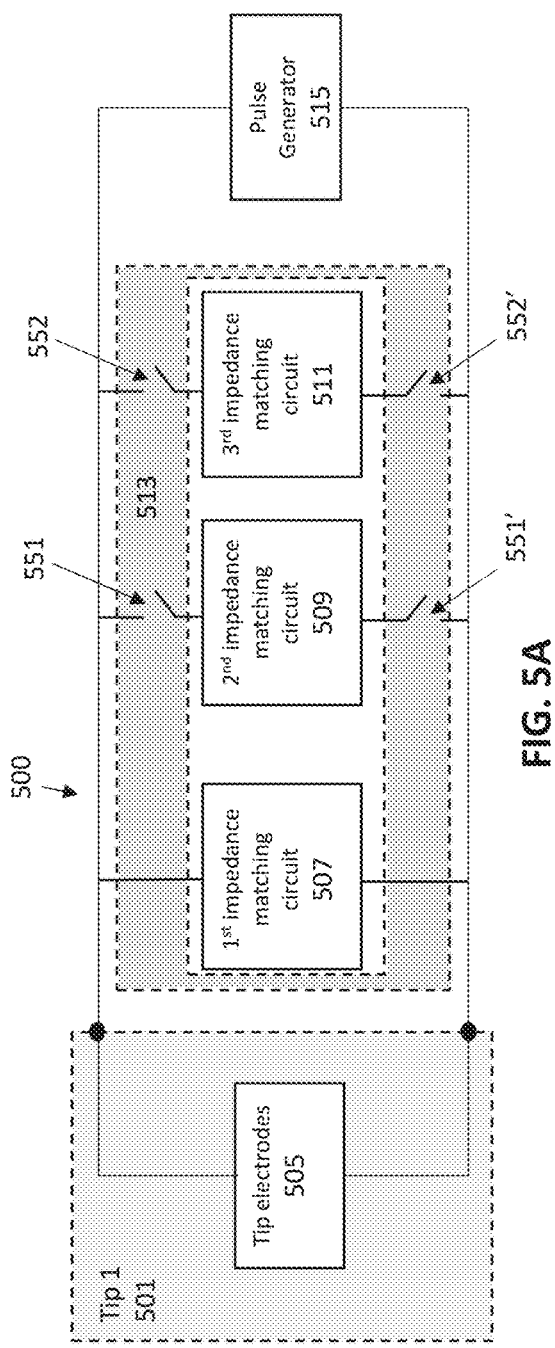
FIG. 5A schematically illustrates one example of an electrical diagram for an apparatus as described herein, showing a tip in electrical communication with a handle and a pulse generator; the handle includes an impedance matching selector.

FIG. 5A schematically illustrates one example of an apparatus 500 in which a first tip (Tip 1) 501, including tip electrodes 505, connected to the apparatus so that the tip is in electrical communication with pulse generator circuitry 515 of the apparatus. The apparatus also includes a plurality of impedance matching circuits, shown in this example as a first impedance matching circuit 507, a second impedance matching circuit 509, and a third impedance matching circuit 511. In some examples fewer (e.g., two) or more (e.g., four, five, six, seven, etc.) impedance matching circuits may be used. The apparatus also includes an impedance matching selector 513 that is shown by the dashed lines surrounding the impedance matching circuits (e.g., mechanical switches). In some examples the first impedance matching circuit is not part of the impedance matching selector (e.g., the handle may include a "default" impedance matching circuit). In FIG. 5A the impedance matching selector 513 engages with the tip (not shown) so that only the first impedance matching circuit 507 is in electrical communication with the electrodes 505 on the tip and the pulse generator. A mechanical engagement (e.g., via a shape encoding connection) between the electrode tip 501 and the handle apparatus (e.g., the handle of the applicator) may place one or more of the impedance matching circuits within the handle in the connection between the electrodes on the tip and the pulse generator. In FIG. 5A only the first impedance matching circuit is shown connected (the second and third impedance matching circuits are shown disconnected, via switches 551, 551', 552, 552' forming part of the impedance matching selector that are opened.

Figure 5B:
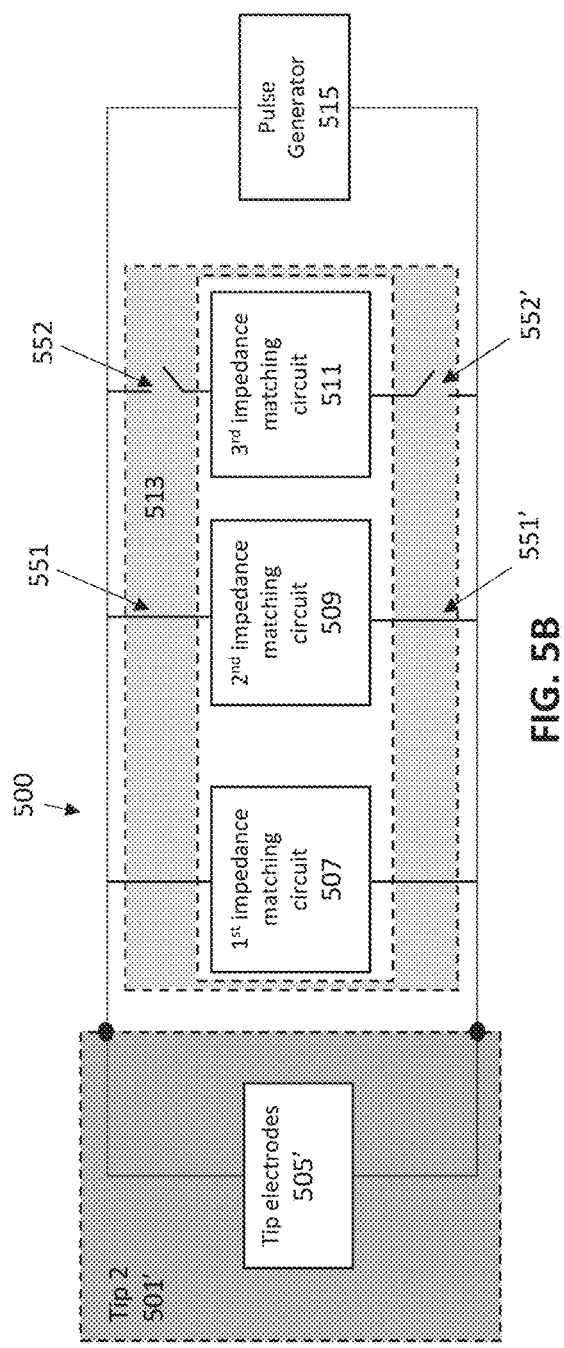
FIG. 5B shows the same example of FIG. 5A with a different electrode tip ("tip 2") connected.

In FIG. 5B the apparatus 500 of FIG. 5A is shown with a different tip (tip 2) 501' attached. In this example, the mechanical connection between the tip 2 and the handpiece causes the impedance matching selector 513 to engage a different (or different set of) one or more of the impedance matching circuits in parallel with the electrical connection between tip 2 and the circuitry generating the pulses (pulse generator circuitry 515). In FIG. 5B, the second impedance matching circuit 509 as well as the first impedance matching circuit 507 are included in the electrical pathway between the tip electrode 505' and the pulse generator circuitry 515, as the impedance matching selector 513 has closed gates 551, 551', placing it in parallel with the tip electrodes of the tip 501', thereby setting the impedance matching circuit, as shown.

In some examples the impedance matching selector may include a displaceable member, such as a plunger 621, as shown and described in FIG. 6. In FIG. 6 the impedance matching selector 613 is housed within the handle and includes a displaceable member, shown in FIG. 6 as a plunger 621 (also shown in FIG. 7 as plunger 721) that is configured to be displaced, for example, by a projection from the electrode tip when the electrode tip is engaged with the handle. In this example, the impedance matching selector forms the open distal face of the handle (see, e.g., FIG. 4) and includes a distal-facing opening 623 on/into which the tip couples. Two or more electrode tip electrical connectors on the tip may engage with handle electrical connectors 625, 625' that are accessible through (and/or may be part of) the impedance matching selector, as shown in FIG. 6. These connectors may be, for example, high-current/high power contacts (e.g., RADSOK high current connectors). In the example shown in FIG. 6, the plunger 621 may travel, e.g., more than 10 mm (e.g., more than 15 mm, more than 19 mm, etc.) and may displace an internal set of connectors that may connect to the electrical pathway between the handle electrical connectors (that are coupled to the electrode tip electrical connectors) and the pulse generator circuitry.

The impedance matching selector shown in FIG. 6 is configured as an open switch (e.g., mechanical switch) that can be driven closed when the correctly keyed (matching) and configured electrode tip engages the handle and drives the plunger 621 distally (not shown) into the housing 602 of the impedance matching selector 613 so that that a set of internal connectors engage to close the mechanical switch, putting a second impedance matching circuit in parallel contact with the pathway between the pulse generator circuitry and the electrode of the electrode tip, as described in FIG. 5, above, thereby adjusting the impedance matching of the electrode tip, based and dependent upon the encoding shape connection with the electrode tip.

For example, FIG. 7 shows a partially exploded view of the impedance matching selector of FIG. 6. In this example, the outer housing 702 of the impedance matching selector encloses and provides a channel for the plunger 721. The plunger is coupled to a bias 725 (shown here as a spring, such as a spring having a preload of about 0.1 lb and a final load of about 1 lb) and is part of a sled 732. The sled also holds a set of internal electrical contacts 727, which in this example are a pair of jumper connects. When the plunger is driven distally by the encoding shape connection, e.g., a protrusion on the electrode tip against the bias, the sled may also be driven distally and the internal electrical contacts 727 are driven within an electrically insulating housing 733 until they contact a complementary set of internal electrical contacts 737 (e.g., another set of pogo pins) that are also housed within the insulating housing 733. This may close the switch(s), placing the downstream impedance matching circuit 741 in parallel with the electrical connection between the electrodes in the electrode tip and the pulse generator circuitry. In FIG. 7, the impedance matching circuit shown includes a pair of resistors (150 Ohm resistors), but other resistor and/or circuit elements may be included. The impedance matching circuit is connected via an additional pair of internal connectors 744 (shown as high current/high voltage connectors). Pogo pins forming part of the internal connector (e.g., internal electrical contact) may be moved to contact a stationary complementary contact to close the switch and place the impedance matching circuit (including the two 150 Ohm resistors) in the electrical pathway between the electrodes of the electrode tip and the pulse generator circuitry, as described above.

In any of the examples described herein the impedance matching selector may be configured to prevent arcing or other electrical failure modes, even when operating at very high currents and/or voltages and high pulsing rates (e.g., microsecond, sub-microsecond, such as nanosecond, etc.). For example as mentioned above, the connectors, and in particular the internal connectors, may be rated for use with high current/high voltage. In FIG. 7, the housing 733 enclosing the first set of internal connectors (e.g., internal electrical contacts 727 and 737) may be electrically insulating channels within the housing 733 formed of a high dielectric material. The configuration of the internal connectors may also be set up so that the arrangement between internal connectors in the "open circuit" (not connected) configuration may include a significant air gap to prevent arcing and may be set some minimum creep distance apart (e.g., at least 10 mm, at least 15 mm, at least 20 mm, at least 25 mm, at least 30 mm, at least 35 mm, at least 40 mm, at least 45 mm, etc.).

For example, FIG. 8A shows a back view of the impedance matching selector 813 (shown in FIG. 8B), showing resistor leads 853 that electrically connect the impedance matching circuit 844 to the complementary set of internal electrical contacts 837 (shown in FIG. 8C). The set of internal electrical contacts 837 couple to the first set of internal electrical contacts 827 when the sled 833 is driven fully proximally when the proper encoding shape connection is made with a complimentary electrode tip. The impedance matching circuit 844 may comprise, for example, a pair of resistors, such as 150 Ohm resistors.

FIG. 8C shows a cut away view of an internal section through the impedance matching selector 813 when the plunger is not engaged and the internal set of connectors 827, 837 (which may be referred to herein as internal electrical contacts) are not engaged but are held apart by the bias (not shown in FIG. 8C). The spacing 861 between the internal connectors 827, 837 is a minimum air gap distance. In the example shown in FIG. 8C, the minimum air gap distance is greater than 10 mm (e.g., approximately 14.3 mm). Further, the minimum clearance distance 855 (shown in bold) is greater than a minimum clearance distance that avoids arcing; in FIG. 8C, the minimum clearance distance is at least twice the sum of the air gap 861 length.

Figure 9A:
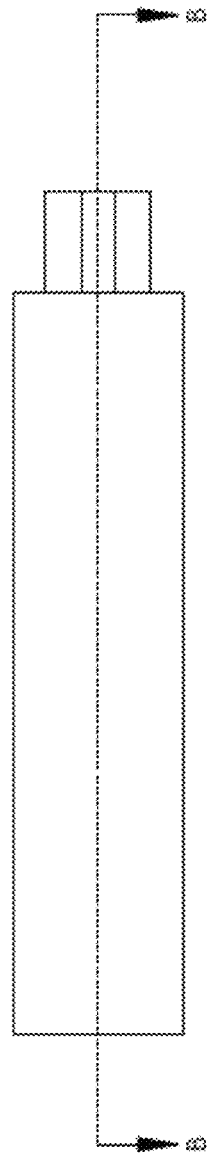
FIG. 9A shows a top view of one example of an impedance matching selector.
Figure 9B:
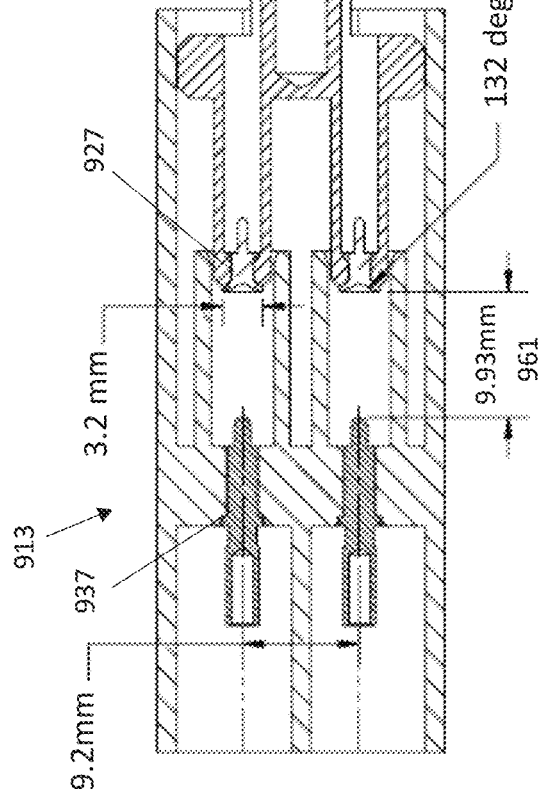
FIG. 9B is a sectional view (along line B-B of FIG. 9A) through the example of a portion of an impedance matching selector of a handle as shown in FIG. 9A.
Figure 10A:
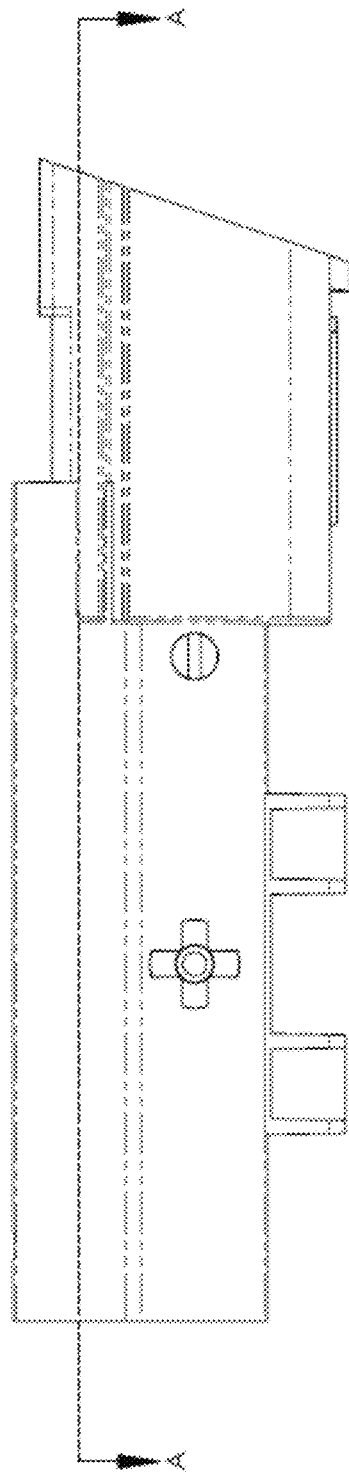
FIG. 10A shows a view of another example of a portion of an impedance matching selector.
Figure 10B:
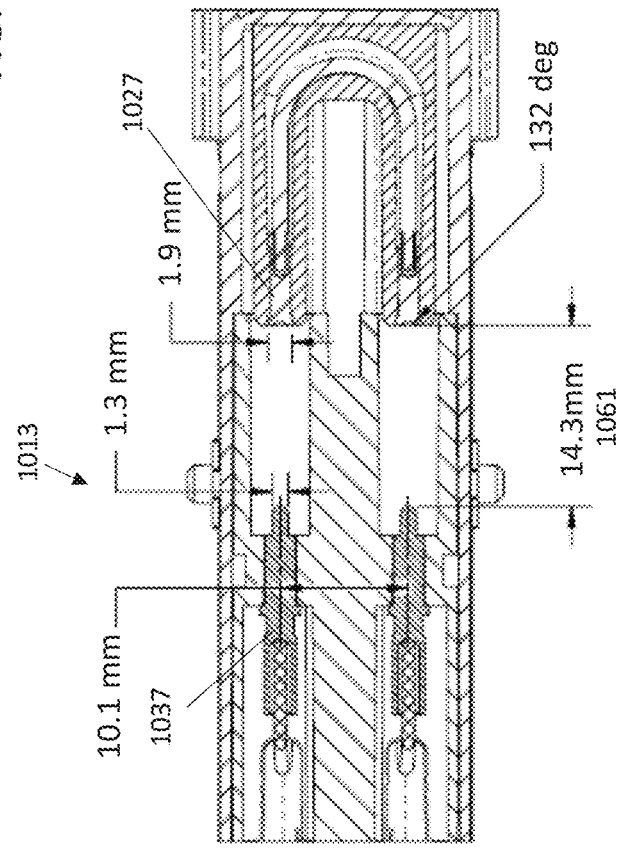
FIG. 10B is a sectional view (through line A-A of FIG. 10A) of the impedance matching selector of a handle as shown in FIG. 10A.

FIGS. 9A-9B and 10A-10B illustrate other examples of sections through a portion of an impedance matching selector 913 and 1013. In FIG. 9B the spacing 961 between the internal connectors 927, 937 (first and second internal electrical contacts) is an air gap having a greater than a minimum air gap distance (in this example, approximately 10 mm). In FIG. 10B the spacing 1061 between the internal connectors 1027, 1037 (first and second internal electrical contacts) of the impedance matching selector 1013 is an air gap having a greater than a minimum air gap distance (e.g., greater than 10 mm, in this example approximately 14.3 mm). In FIGS. 9B and 10B the dimensions shown for the internal connector(s) are merely examples that are intended to be illustrative and should not be considered limiting.

Figure 11B:
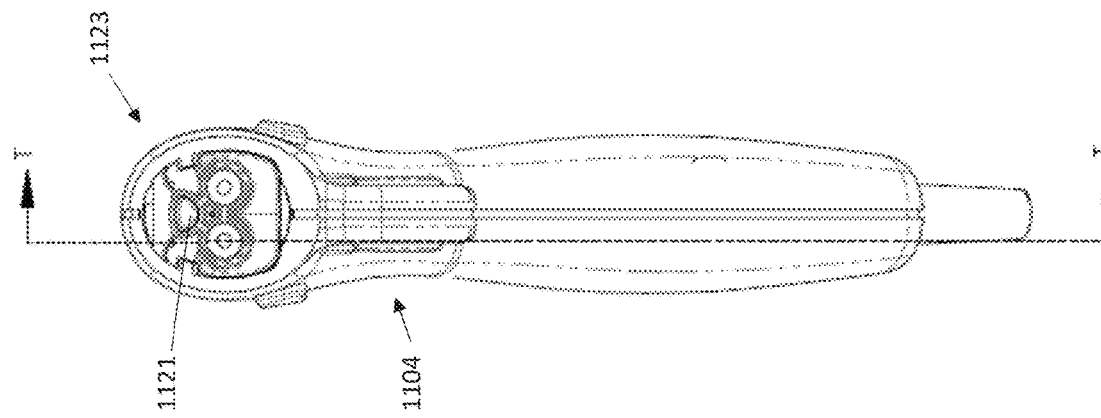
FIG. 11B is shows an end view of the handle shown in FIG. 11A.
Figure 11A:
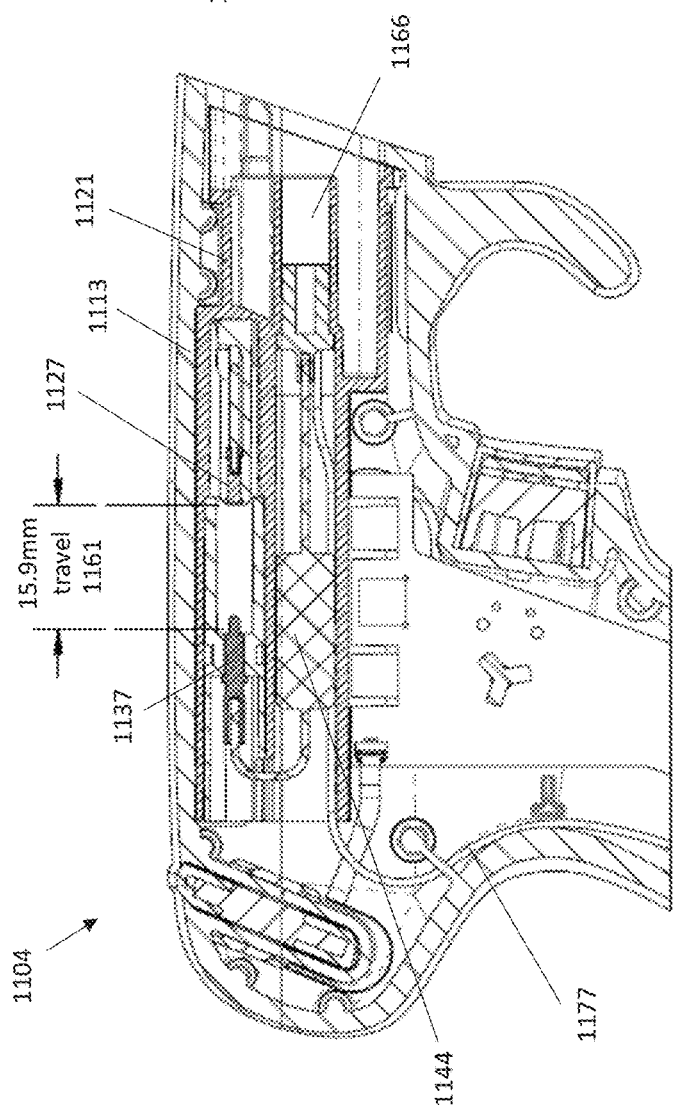
FIG. 11A is a cross section through one example of a handle including an impedance matching selector.

FIG. 11A shows an example of a cross-sectional view of a handle portion of a treatment applicator for use with a pulse generator that includes an impedance matching selector similar to that shown in FIGS. 6-10B above. In this example, the handle 1104 includes an impedance matching selector 1113 at the distal end. The impedance matching selector includes a plunger 1121 and a set of internal connectors, including a first internal electrical contact 1127 and a second internal electrical contact 1137. The first set of internal electrical contacts is coupled to the displaceable sled that may move when the plunger 1121 is displaced by engaging an encoding shape connection on the electrode tip. The second set of internal electrical contacts is statically held and is connected to the impedance matching circuit (e.g., impedance matching resistor 1144). The impedance matching circuit is coupled to the handle electrical connector 1166 for receiving the electrode tip electrical connectors, but the impedance matching circuit is open (unconnected) until the internal mechanical switch is closed by driving the plunger proximally, as described above, to close the air gap travel distance 1161 and connect the internal connector. In FIG. 11A, the handle electrical connector 1166 is also attached to a wire (e.g., a high-voltage wire 1177) and/or a first impedance matching circuit that connects the handle electrical connector to the pulse generator. FIG. 11B shows a front view of the handle of FIG. 11A, showing the distal opening 1123.

Figure 12:
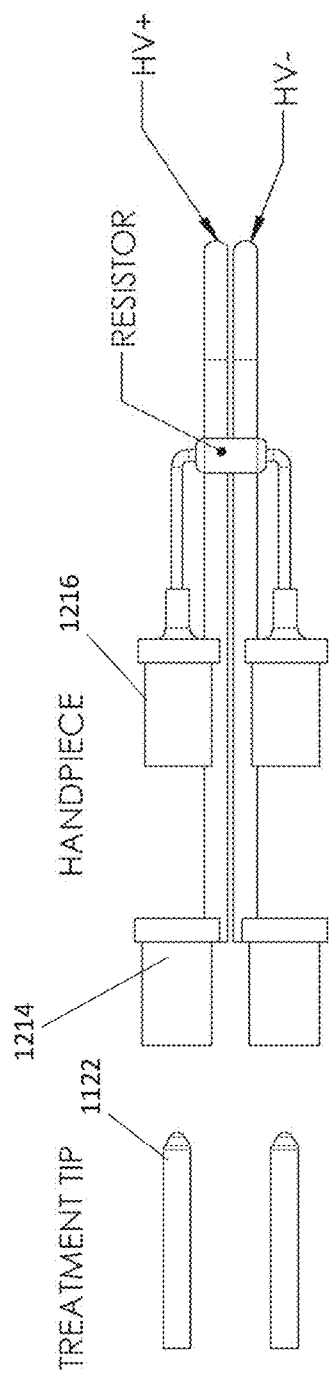
FIG. 12 schematically illustrates an example of an impedance matching selector in which the encoding shape connection from the electrode tip comprises pins (conductive pins) of different lengths.

In some examples the impedance matching selector does not include a displaceable member, but is instead fixed within the handle, and the electrode tip electrical connectors form the encoding shape connection to the impedance matching selector. In this example the impedance matching selector includes sets of internal connectors that are spaced apart and may each connect to one or more impedance matching circuits. For example, FIG. 12 illustrates one example of a schematic showing an impedance matching selector having two pairs of internal connectors (contacts) 1214, 1216 that are each configured to receive (and make contact with) an electrode tip electrical connector; the electrode tip electrical connector is configured as a pin 1122. In FIG. 12, the pins may be long enough so that they may pass through the first set of internal contacts 1214 and extend to the second set of internal contacts 1216 (in some examples additional internal contacts may be included along the line of travel of the contacting pin to facilitate additional contacts with other circuit elements). In some examples the pin may be short, so that it only connects to the first set of internal contacts 1214. The first set of internal contacts (and in some examples, the second or additional sets of internal contacts) may be annular, so that the pin may pass through the internal contact; alternatively the internal contact may only be partially annular or may only make contact partially around (and against) the pin. The first set of internal contacts 1214 may connect to a first impedance matching circuit and/or the circuitry for the pulse generator (shown by HV+ and HV−). The second (and any subsequent) internal contacts 1216 may connect to a second impedance matching circuit (shown here as impedance matching resistor, R).

Thus, in FIG. 12, the impedance matching selector is configured by arranging the internal connectors (for example, selecting a particular impedance matching circuit elements according to the length or other dimensions of the internal connectors), which may be coupled to one or more impedance matching circuits, in a spaced apart configuration that may be connected by pins of the appropriate encoding shape length. Thus, an encoding shape connection formed by the pins of the electrode tip (e.g., the electrode tip electrical connectors) and the internal contacts may set the impedance matching for the tip based on which impedance matching circuits are engaged by the impedance matching selector.

FIGS. 13A-13B, 13C-13D and 13E-F illustrate examples of examples of an impedance matching selector configured as illustrated schematically in FIG. 12. For example, in FIG. 13B the impedance matching selector includes a first set of internal connectors 1314 and second set of internal connectors 1316 that are arranged in a line with an air gap between them. The air gap (and the clearance path between them) may be selected as described above to have a minimum clearance distance (e.g., 10 mm or greater, 15 mm or greater, etc.) to prevent or minimize arcing.

Figure 13A:
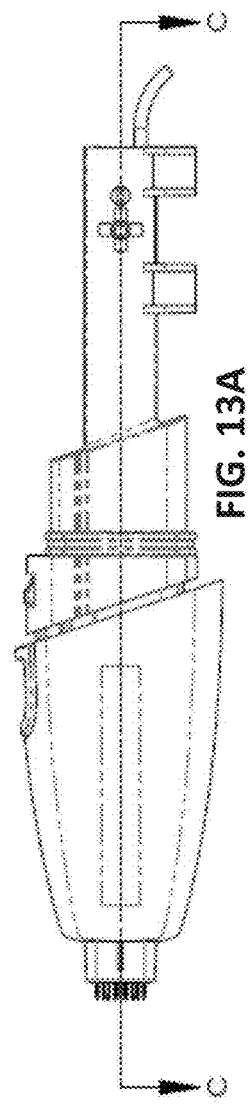
FIG. 13A shows a side view of a portion of a handle of a treatment applicator.
Figure 13B:
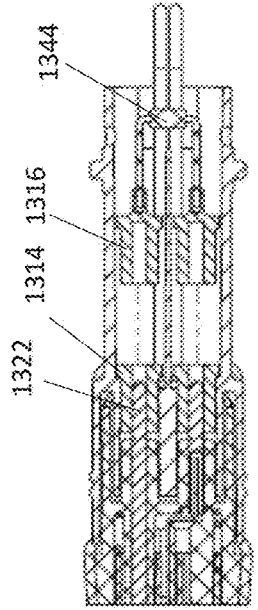
FIG. 13B shows a section (along line C-C) through the example of a handle of the treatment applicator having an impedance matching selector shown in FIG. 13B, which is similar to that shown schematically in FIG. 12 with different encoding shape connectors (e.g., shown in this example as pins of different length) engaging with the internal connectors of the impedance matching selector.
Figure 13C:
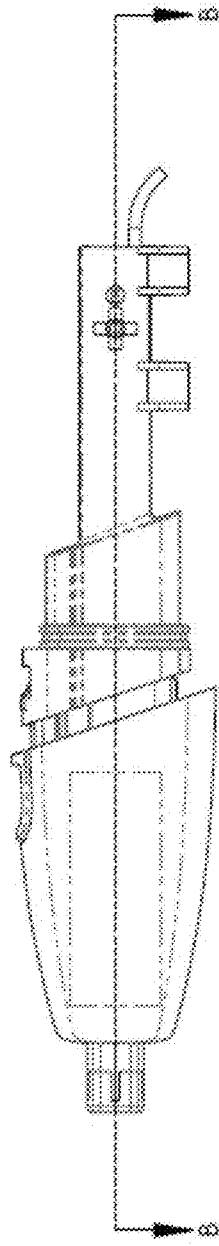
FIG. 13C shows a side view of an example of a portion of a handle including an impedance matching selector.
Figure 13D:
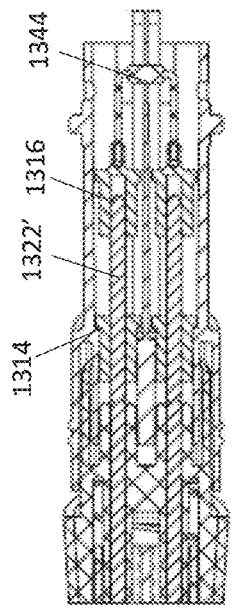
FIG. 13D shows a section (along line B-B) of the example of a handle shown in FIG. 13C, in which the encoding shape connectors comprise long pins that connect to both sets of internal connectors.
Figure 13E:
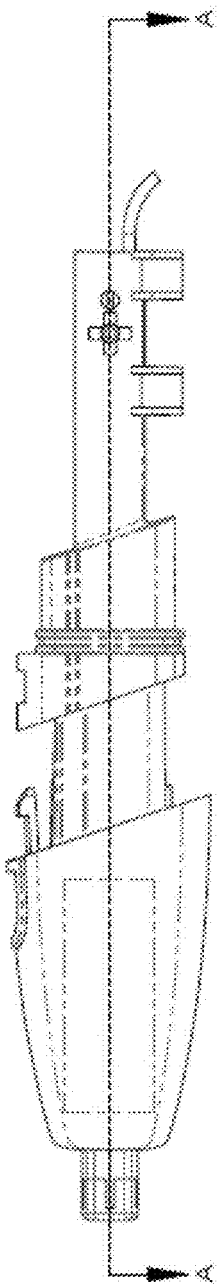
FIG. 13E shows another example of a portion of a handle including an impedance matching selector.
Figure 13F:
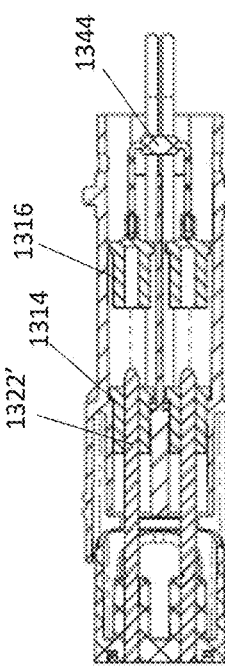
FIG. 13F is a section (along line A-A) of the exemplary portion of the handle shown in FIG. 13E, showing an encoding shape connection when the tip being inserted into the handpiece/handle (shown here as the pins forming the electrical connectors).

In FIG. 13B the pins 1322 (e.g., the electrode tip electrical connectors) are both short, so that only the first set of internal connectors 1314 are connected to them. In FIG. 13D the pin 1322' is longer and passes through the first internal connector 1314 (e.g., annular), making this first electrical connection (e.g., with a first impedance circuit), and then continuing on to also contact the second set of internal connectors 1316, completing the circuit to put the second impedance matching circuit elements, e.g., 1344, in parallel with the first internal connection and therefore the electrode tip, as shown. FIG. 13F illustrates insertion of the electrode tip electrical connectors (e.g., the pins) shown in FIG. 13D.

Figure 14:
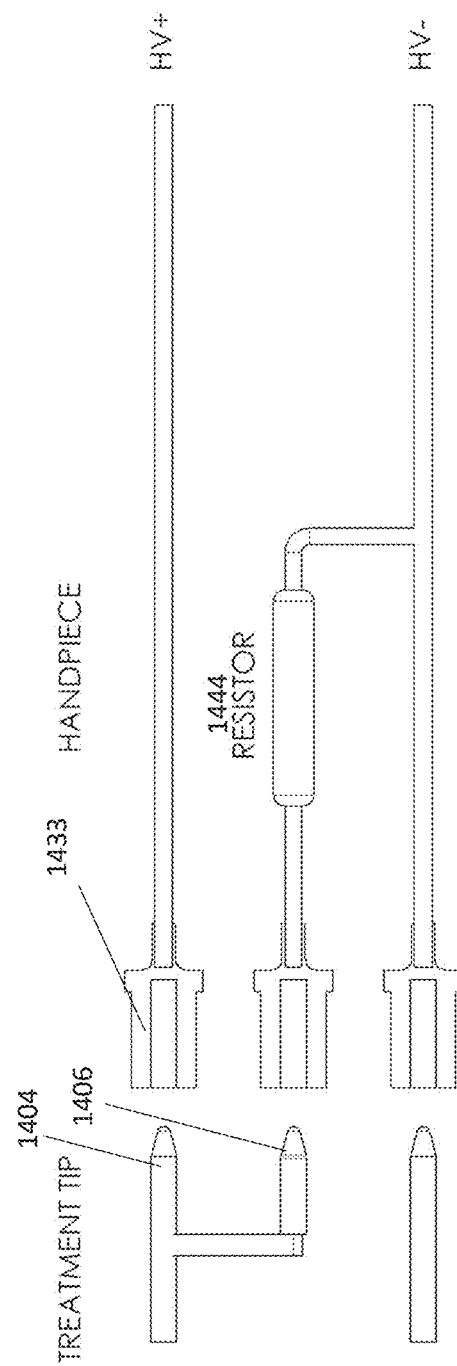
FIG. 14 schematically illustrates the encoding shape connection of the handle, including the impedance matching selector and the posts/pins extending from the electrode tip.

FIG. 14 illustrates another example of an impedance matching selector similar to that shown in FIG. 11A, above. This configuration includes three pins that may be keyed to form the encoding shape connection between the electrode tip and the pulse generator circuitry. The three (or more) pins may be the same length, rather than relying on pins of different length to make different connections with the internal connectors of the impedance matching selector. For example in FIG. 14 the upper pin or conductor of the electrode tip connector is bifurcated into two pins (a first pin 1404 and a second pin 1406) to make connections with either a first matching connector (e.g., a handle electrical connector 1433); or when the second pin is present, it may make connection with a second impedance matching circuit 1444 (shown as impedance matching resistor, R). A third pin completes the connection with the first impedance matching circuit and/or pulse generator (e.g., HV−).

FIGS. 15A-15C and 16A-16C show examples of tips and handles configured so that the impedance matching selector is based on the number, position and/or length of the pins (electrode pins or connectors) when the tip engages with the handle. For example, in FIGS. 15A-15C and 16A-16C, the apparatus is similar to the one shown schematically in FIG. 14. In this example the pins extend from the proximal end of the electrode tip 1501 or 1601, and include a first pin 1504 or 1604, a second pin 1606 and (in some examples) a third pin 1508 or 1608. The first pin 1604 is electrically continuous with the second pin 1606. In FIG. 15A the tip includes only a first pin and a third pin; thus the second pin is not present and does not connect with an internal connector (shown in FIGS. 16A-16B) and, therefore, the second impedance matching circuit (e.g., impedance matching resistor 1544).

In contrast, FIG. 16B shows an example in which all three pins are present. The second pin 1606 makes electrical contact with the internal connector so that the second impedance matching circuit (e.g., impedance matching resistor) 1544 is connected in parallel with the connection between the tip electrodes and the pulse generator circuitry. FIG. 16B illustrates an example of a configuration similar to the one shown in FIG. 15B, but with the electrode tip 1601 having 3 pins 1604, 1606, 1608, and shown disengaged from the handle connector 1620. In FIG. 16B, which is similar to the configuration shown in FIG. 15B, the tip 1601 is engaged with the handle connector 1620, so that the encoding shape connection is made by the electrode tip electrical connectors.

Figure 17:
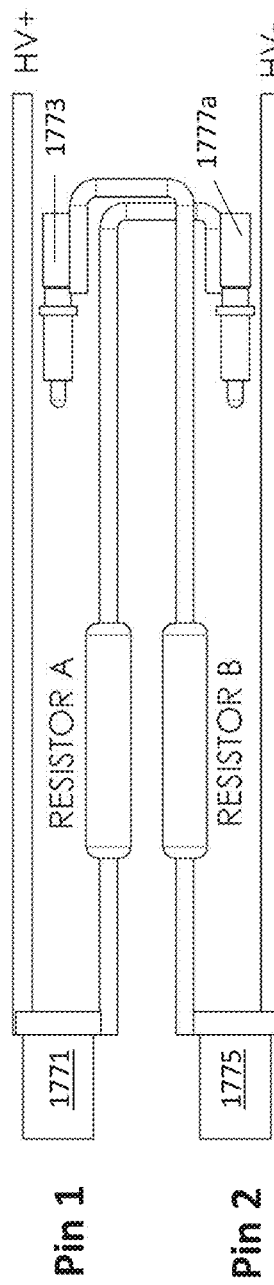
FIG. 17 illustrates one example of a schematic for an impedance matching selector portion of a handle with cross-wired resistors.

In some examples multiple different impedance matching circuits may be selected by the impedance matching selector based on one or more encoding shape engagements between the electrode tip and the impedance matching selector. FIG. 17 schematically illustrates an example of a configuration in which the impedance matching selector includes a plurality of internal contacts, similar to that shown in FIG. 11A, but with cross-connected impedance matching circuits. For example, in FIG. 17, four internal connectors are shown. A first internal connector 1771 and a third internal connector 1773 may be configured as annular connectors, while a second internal connector 1775 and a fourth internal connector 1777a may be annular or not (e.g., shown as pins in FIG. 17). Each internal connector is connected to an impedance matching circuit and these circuits are cross-connected (e.g., the first and fourth connectors are connected, the second and third connectors are connected, etc.).

Figure 18F:
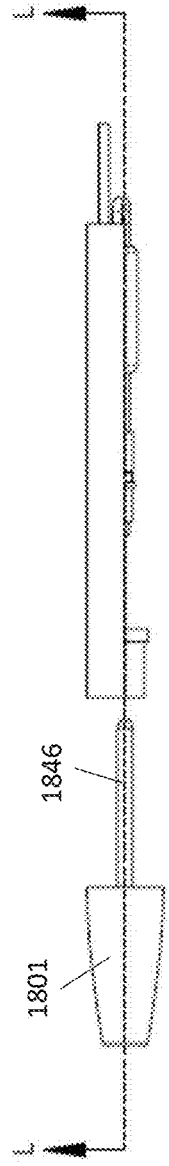
FIG. 18F shows an electrode tip and an impedance matching selector portion of a handle.
Figure 18G:
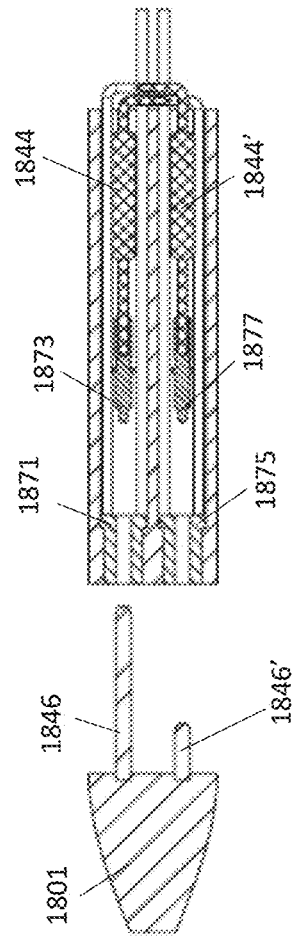
FIG. 18G is an example of a section ((along line L-L of FIG. 18F) through the electrode tip and impedance matching selector portion of a handle of FIG. 18F, showing the electrode tip (having an encoding shape connection including a long pin and a short pin) ready to engage with the impedance matching selector portion.
Figure 18A:
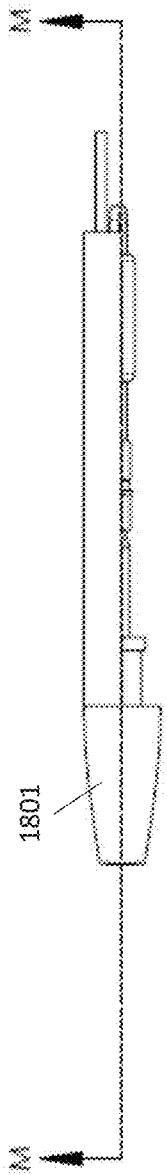
FIG. 18A shows one example of an electrode tip coupled with an impedance matching selector portion of a handle, as described herein.

FIGS. 18A-18G illustrate the use of an apparatus such as that shown schematically in FIG. 17. FIG. 18A shows a portion of a handle and a tip disconnected from each other, FIG. 18F shows a portion of a handle and a tip connected to each other, while FIGS. 18B-18E illustrate different configuration for engage a tip to the handle to select the impedance matching to the particular tip configurations shown.

Figure 18B:
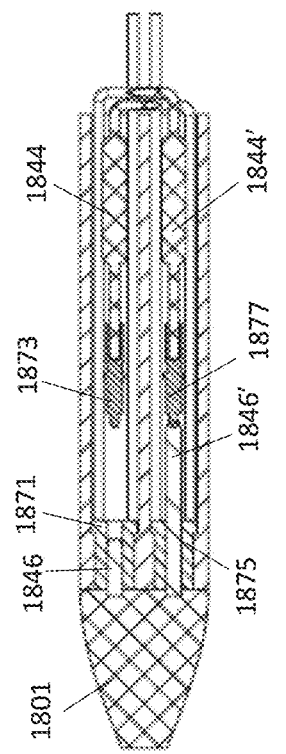
FIG. 18B shows one example of a section through an electrode tip coupled with an impedance matching selector portion of a handle, as described herein.
Figure 18D:
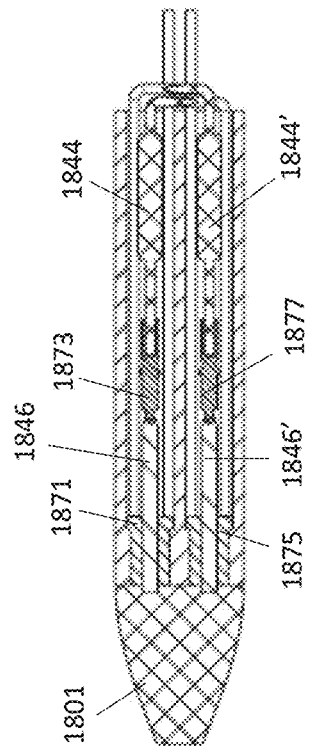
FIG. 18D is an example of a section through an electrode tip coupled with an impedance matching selector portion of a handle, in which the encoding shape connection of the electrode tip includes a short pin and a long pin.
Figure 18C:
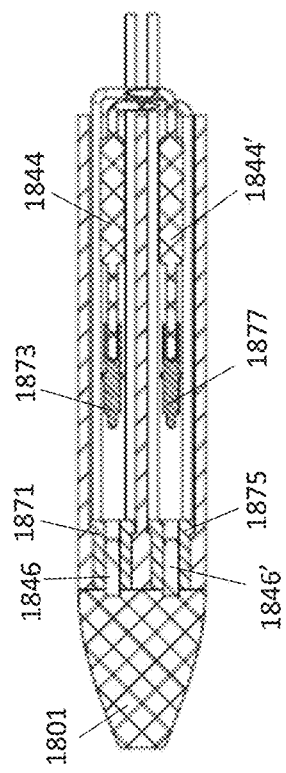
FIG. 18C is an example of a section through an electrode tip coupled with an impedance matching selector portion of a handle, in which the encoding shape connection of the electrode tip includes a long pin and a short pin.
Figure 18E:
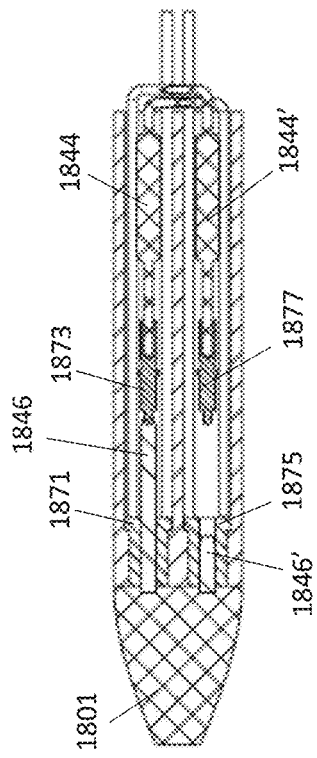
FIG. 18E is an example of a section through an electrode tip coupled with an impedance matching selector portion of a handle, in which the encoding shape connection of the electrode tip includes two long pins and two resistors connected.

In FIG. 18B, when both pins 1846, 1846' of the electrode tip 1801 are short and the electrode tip is coupled with the handle, no additional impedance matching circuit elements are connected between the electrodes of the electrode tip and the pulse generator circuitry. In FIG. 18C, the first pin 1846 is long and contacts both a first internal connector 1871 and a second internal connector 1873 while the second pin 1846' is short and only contacts a third internal connector 1875; this configuration connects only the second impedance matching circuit elements (e.g., 1844) in parallel with the connection between the electrode tip and the pulse generator circuitry (e.g., setting the impedance matching of the tip). In FIG. 18D, the first pin 1846 is short and contacts only the first internal connector 1871 but not the second internal connector 1873, while the second pin 1846' is long and contacts both the third internal connector 1875 and the fourth internal connector 1877; this configuration connects only the third impedance matching circuit 1844' in parallel with the connection between the electrode tip and the pulse generator circuitry. In FIG. 18E, both the first pin 1846 and the second pin 1846' are long; the first pin 1846 contacts both the first internal connector 1871 and second internal connector 1873 and the second pin 1846' contacts both the third internal connector 1875 and the fourth internal connector 1877; this configuration connects both the second impedance matching circuit 1844 and the third impedance matching circuit 1844' in parallel with the connection between the electrode tip and the pulse generator circuitry. FIG. 18G illustrates insertion of a tip such as the electrode tip shown in FIG. 18C.

Figure 19:
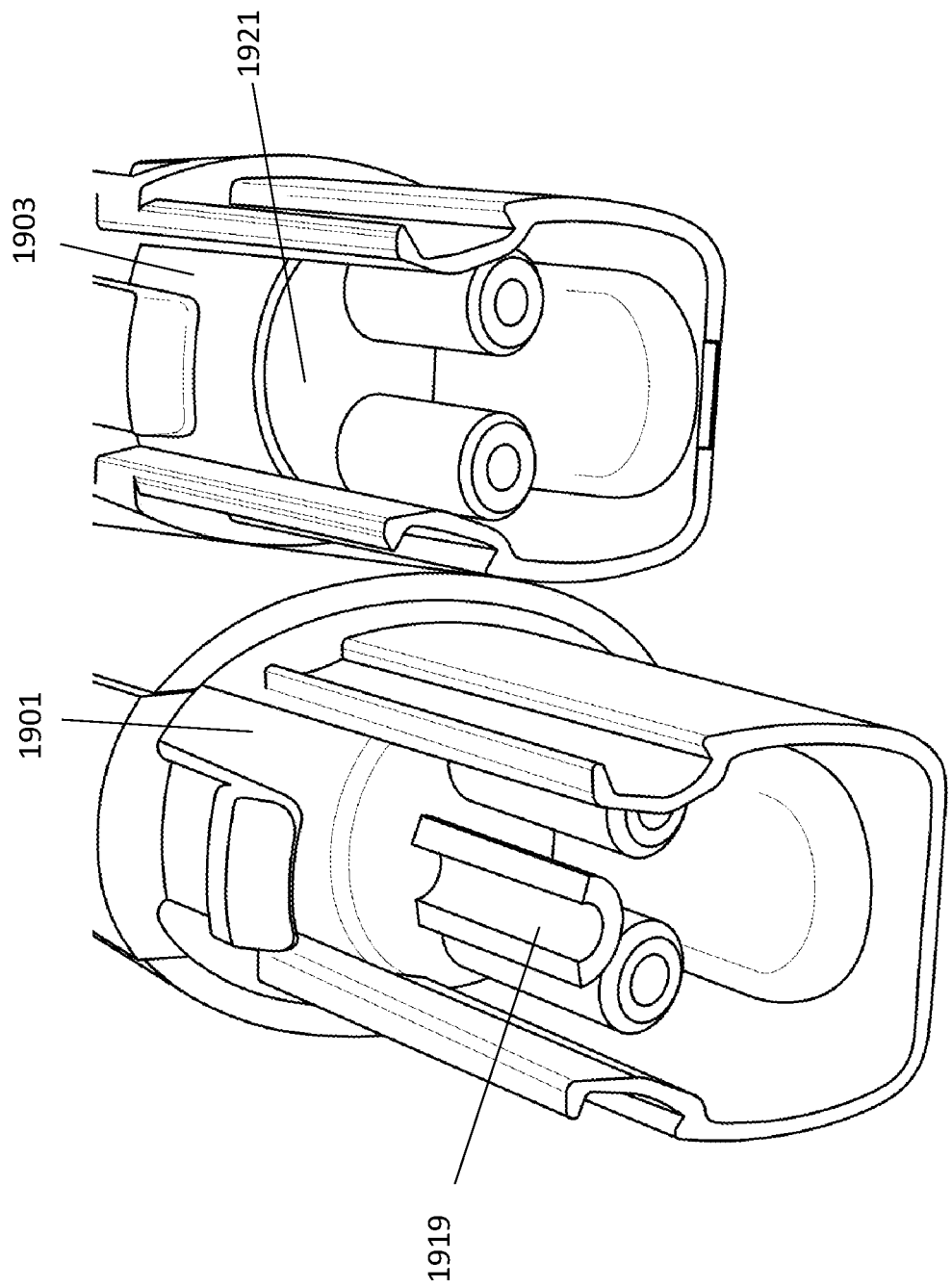
FIG. 19 is an example showing a distal end region of two electrode tips (one with a plunger and the other without a plunger) as described herein.

FIG. 19 illustrates examples of electrode tips having different keying, with and without a displaceable member. In FIG. 19 the tip on the left (1901) includes a protrusion (e.g., a post or plunger 1919) that is configured to push and engage the impedance matching selector on the handle. Separately, electrode tip electrical conductors (not shown in FIG. 19) may make electrical contact with handle electrical connectors, which may be part of the impedance matching selector, or separate. In FIG. 19, the tip on the right (1903) does not include a displaceable member, such as protrusion and is flat in this region 1921.

Any of the apparatuses described herein may be used as part of a method for automatically and/or mechanically setting the impedance matching for a variety of different electrode tips. For example, FIG. 20 illustrates an example of a method 2000 of selecting an impedance circuit for a removable electrode tip of a treatment or pulse applicator. In FIG. 20, the method includes coupling (e.g., removably coupling) a first electrode tip to a handle of an applicator (step 2001). The electrode tip may be electrically and/or mechanically coupled. Coupling may include engaging a first connector (encoding shape connector) from the first electrode tip with an impedance matching selector of the handle, wherein the impedance matching selector selectively places at least one electrode tip electrical connector of the first electrode tip in electrical communication with one or more impedance matching circuits based on the first encoding shape connector (step 2003). This will allow a pulse generator to be in electrical communication with a plurality of electrodes in the first electrode tip through the selected one or more impedance matching circuits. This may further include, in some examples, electrically isolating each of the impedance matching circuits within the handle to prevent arcing. This may be accomplished by maintaining a minimum clearance distance between a) internal electrical contacts of the impedance matching selector that are in electrical communication with the at least one electrode tip electrical connector and b) internal electrical connectors of the impedance matching selector that are in electrical communication with any of the impedance matching circuit elements not selected by the impedance matching selector to be in electrical communication with the at least one electrode tip electrical connector of the electrode tip (step 2005).

Although the methods and apparatuses described herein focus primarily on removably coupling an electrode tip to a handle of an applicator, any of these methods and apparatuses may instead be used for irreversibly coupling an electrode tip to a handle or applicator; for example in some examples the handle may be single-use or limited use (including disposable).

In some examples, the method may optionally include applying a pulsed electrical energy from the first electrode tip (step 2007). In any of the methods described herein, the application of the pulse electrical energy may be for cosmetic and/or for therapeutic purposes. In some examples these methods may be strictly for cosmetic purposes, e.g., to treat any cosmetic defect or condition, such as a blemish.

Optionally, any of these methods may further include removing the electrode tip and applying another, different, electrode tip (step 2009); the handle of the pulse applicator may again automatically set the impedance matching for the tip based on the encoding shape between the different electrode tip and the handle (e.g., between the electrode tip and an impedance matching selector in the handle).

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments and examples may be included in some embodiments/examples and not in others, and some feature(s) described in reference to one example may be incorporated in the other provided examples. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An applicator handle for high voltage pulsing, the applicator handle comprising:
   a plurality of impedance matching circuits;
   a plurality of handle electrical connectors configured to engage with a plurality of electrode tip electrical connectors on an electrode tip so that a plurality of electrodes of the electrode tip are in electrical communication with a pulse generator; and
   an impedance matching selector configured to selectively couple the plurality of electrode tip electrical connectors with one or more of the impedance matching circuits of the plurality of impedance matching circuits based on an encoding shape connection with the electrode tip, wherein the impedance matching selector comprises a first set of internal electrical contacts comprising high-current/high power contacts separated from a second set of internal electrical contacts by a minimum clearance distance that avoids arcing and wherein the first set of internal electrical contacts is configured to couple with the second set of internal contacts to engage one or more of the plurality of impedance matching circuits when the encoding shape connects with the electrode tip.

2. The handle of claim 1, wherein the encoding shape connection comprises a protrusion extending from the electrode tip into the handle.

3. The handle of claim 1, wherein the encoding shape connection comprises a plurality of pins forming the plurality of electrode tip electrical connectors.

4. The handle of claim 1, wherein at least some of the plurality of impedance matching circuits share one or more circuit components.

5. The handle of claim 1, wherein the plurality of impedance matching circuits is arranged so that the impedance matching circuits may each be connected in parallel by the impedance matching selector.

6. The handle of claim 1, wherein at least one of the plurality of impedance matching circuits comprises a resistor configured to be arranged in parallel between two or more of a plurality of electrode tip electrical conductors.

7. The handle of claim 1, wherein the impedance matching selector comprises a plunger configured to be displaced by the encoding shape connection with the electrode tip.

8. The handle of claim 1, wherein the first set of internal electrical contacts is in electrical communication with the pulse generator forming a first impedance matching circuit of the plurality of impedance matching circuits and the second set of internal electrical contacts is in electrical communication with a second impedance matching circuit of the plurality of impedance matching circuits.

9. The handle of claim 8, wherein the second set of electrical contacts is configured to be displaced by the impedance matching selector to place the second impedance matching circuit in parallel with the first impedance matching circuit based on the encoding shape connection with the electrode tip.

10. The handle of claim 1, wherein the minimum clearance distance is 10 mm or greater.

11. The handle of claim 1, wherein the plurality of handle electrical connectors form a part of the impedance matching selector.

12. The applicator handle of claim 1, wherein the minimum clearance distance is at least twice an air gap length between the first set of internal electrical contacts and the second set of internal electrical contacts.

13. The applicator handle of claim 1, wherein the first set of internal electrical contacts is on a displaceable sled and is configured to couple with the second set of internal contacts to engage one or more of the plurality of impedance matching circuits when the encoding shape connection displaces the displaceable sled.

14. An applicator for high voltage pulsing, the applicator comprising:
   a removable electrode tip, the removable electrode tip comprising:
      a plurality of electrodes, and
      at least one electrode tip electrical connector in communication with the plurality of electrodes;
   a plurality of impedance matching circuits;
   a handle, the handle comprising
   a plurality of handle electrical connectors configured to engage with the at least one electrode tip electrical connector so that the plurality of electrodes of the removable electrode tip are in electrical communication with a pulse generator; and
   an impedance matching selector configured to selectively couple the at last one electrode tip electrical connector with one or more of the impedance matching circuits of the plurality of impedance matching circuits based on an encoding shape connection with the removable electrode tip, wherein the impedance matching selector comprises a first set of internal electrical contacts comprising high-current/high power contacts separated from a second set of internal electrical contacts by a minimum clearance distance that avoids arcing, and wherein the first set of internal electrical contacts is configured to couple with the second set of internal contacts to engage one or more of the plurality of impedance matching circuits when the encoding shape connects with the electrode tip.

15. The applicator of claim 14, wherein the plurality of impedance matching circuits is within one or a combination of: the removable electrode tip, the handle, or the pulse generator.

16. The applicator of claim 14, further comprising a second removable electrode tip configured to form an encoding shape connection with the impedance matching selector that is different from the encoding shape connection of the removable electrode tip.

17. The applicator of claim 14, wherein the encoding shape connection comprises a protrusion extending from the removable electrode tip into the handle or a plurality of pins forming the at least one electrode tip electrical connector.

18. The applicator of claim 14, wherein the impedance matching selector comprises a plunger configured to be displaced by the encoding shape connection with the removable electrode tip.

19. The applicator of claim 14, wherein the handle comprises a handle body housing the plurality of impedance matching circuits and the impedance matching selector, further wherein the handle body housing comprises a grip configured to be hand-held.

20. The applicator of claim 14, wherein the minimum clearance distance is 10 mm or greater.

21. A system, the system comprising:
a pulse generator configured to deliver microsecond or sub-microsecond pulses having a voltage of 1 kV or greater;
a removable electrode tip, the removable electrode tip comprising
a plurality of electrodes, and
a plurality of electrode tip electrical connectors in communication with the plurality of electrodes;
a handle, the handle comprising a plurality of handle electrical connectors configured to engage with the plurality of electrode tip electrical connectors so that the plurality of electrodes of the removable electrode tip are in electrical communication with the pulse generator;
a plurality of impedance matching circuits; and
an impedance matching selector configured to selectively couple the plurality of electrode tip electrical connectors with one or more of the impedance matching circuits of the plurality of impedance matching circuits based on an encoding shape connection with the removable electrode tip, wherein the impedance matching selector comprises a first set of internal electrical contacts comprising high-current/high power contacts separated from a second set of internal electrical contacts by a minimum clearance distance that avoids arcing and wherein the first set of internal electrical contacts is configured to couple with the second set of internal contacts to engage one or more of the plurality of impedance matching circuits when the encoding shape connects with the electrode tip.

22. The system of claim 21, wherein the plurality of impedance matching circuits is within one or a combination of: the removable electrode tip, the handle, or the pulse generator.

23. The system of claim 21, wherein the plurality of impedance matching circuits is within the handle.

24. The system of claim 21, wherein the plurality of impedance matching circuits is arranged so that the impedance matching circuits may each be connected in parallel by the impedance matching selector.

25. The system of claim 21, wherein at least some of the impedance matching circuits of the plurality of impedance matching circuits share one or more circuit components.

26. The system of claim 21, wherein the first set of internal electrical contacts is in electrical communication with the pulse generator forming a first impedance matching circuit of the plurality of impedance matching circuits and the second set of internal electrical contacts is in electrical communication with a second impedance matching circuit of the plurality of impedance matching circuits.

27. The system of claim 26, wherein the second set of internal electrical contacts is configured to be displaced by the impedance matching selector to place the second impedance matching circuit in parallel with the first impedance matching circuit based on the encoding shape connection with the removable electrode tip.

* * * * *